US011852802B2

(12) United States Patent
Swanson

(10) Patent No.: US 11,852,802 B2
(45) Date of Patent: Dec. 26, 2023

(54) OPTICAL INSTRUMENT FOR IMAGING AND SENSING USING MULTICORE FIBER

(71) Applicant: Eric Swanson, Gloucester, MA (US)

(72) Inventor: Eric Swanson, Gloucester, MA (US)

( * ) Notice: Subject to any disclaimer, the term of this patent is extended or adjusted under 35 U.S.C. 154(b) by 0 days.

(21) Appl. No.: 17/676,129

(22) Filed: Feb. 19, 2022

(65) Prior Publication Data

US 2022/0221708 A1 Jul. 14, 2022

Related U.S. Application Data

(60) Continuation of application No. 16/704,851, filed on Dec. 5, 2019, now Pat. No. 11,256,080, which is a
(Continued)

(51) Int. Cl.
| | |
|---|---|
| *G02B 23/26* | (2006.01) |
| *G02B 6/02* | (2006.01) |
| *G02B 23/24* | (2006.01) |
| *A61B 1/00* | (2006.01) |
| *G02B 6/28* | (2006.01) |
| *G02B 6/35* | (2006.01) |
| *G02B 6/32* | (2006.01) |

(Continued)

(52) U.S. Cl.
CPC ............ *G02B 23/26* (2013.01); *A61B 5/0066* (2013.01); *A61B 5/0084* (2013.01); *G02B 6/0008* (2013.01); *G02B 6/02042* (2013.01); *G02B 6/2861* (2013.01); *G02B 6/32* (2013.01); *G02B 6/34* (2013.01); *G02B 6/3548* (2013.01); *G02B 6/3586* (2013.01); *G02B 6/425* (2013.01); *G02B 23/2423* (2013.01); *G02B 23/2469* (2013.01); *A61B 1/00096* (2013.01); *A61B 1/00167* (2013.01); *A61B 1/00172* (2013.01); *A61B 5/0068* (2013.01); *A61B 5/0075* (2013.01); *G02B 2006/0098* (2013.01)

(58) Field of Classification Search
CPC ....... A61B 5/0084; A61B 5/0066; A61B 1/07; A61B 1/00165; A61B 1/00167; A61B 1/0017; G01B 9/02091; G01B 9/02004; G02B 6/02042
See application file for complete search history.

(56) References Cited

U.S. PATENT DOCUMENTS

| | | |
|---|---|---|
| 5,041,108 A | 8/1991 | Fox et al. |
| 5,212,743 A | 5/1993 | Heismann |

(Continued)

FOREIGN PATENT DOCUMENTS

| | | |
|---|---|---|
| EP | 0 981 733 B1 | 2/2004 |
| EP | 0 883 793 B1 | 11/2007 |

(Continued)

OTHER PUBLICATIONS

Quack, N., et al., "MEMS-Enabled Silicon Photonic Integrated Devices and Circuits", IEEE Journal of Quantum Electronics, vol. 56, No. 1, pp. 1-10.

(Continued)

*Primary Examiner* — Omar R Rojas
(74) *Attorney, Agent, or Firm* — Rauschenbach Patent Law Group, PLLC; Kurt Rauschenbach

(57) ABSTRACT

Disclosed herein are configurations for fiber optic endoscopes employing fixed distal optics and multicore optical fiber.

12 Claims, 17 Drawing Sheets

Related U.S. Application Data division of application No. 15/147,775, filed on May 5, 2016, now abandoned.

(60) Provisional application No. 62/166,154, filed on May 26, 2015, provisional application No. 62/163,532, filed on May 19, 2015, provisional application No. 62/163,522, filed on May 19, 2015, provisional application No. 62/157,131, filed on May 5, 2015.

(51) Int. Cl.
| | |
|---|---|
| G02B 6/34 | (2006.01) |
| G02B 6/42 | (2006.01) |
| A61B 5/00 | (2006.01) |
| F21V 8/00 | (2006.01) |
| G02B 6/00 | (2006.01) |

(56) References Cited

U.S. PATENT DOCUMENTS

| | | | |
|---|---|---|---|
| 5,321,501 | A | 6/1994 | Swanson et al. |
| 5,459,570 | A | 10/1995 | Swanson et al. |
| 5,465,147 | A | 11/1995 | Swanson |
| 5,956,355 | A | 9/1999 | Swanson et al. |
| 6,134,003 | A | 10/2000 | Tearney et al. |
| 6,160,826 | A | 12/2000 | Swanson et al. |
| 6,191,862 | B1 | 2/2001 | Swanson et al. |
| 6,288,784 | B1 | 9/2001 | Hitzenberger et al. |
| 6,445,939 | B1 | 9/2002 | Swanson et al. |
| 6,485,413 | B1 | 11/2002 | Boppart et al. |
| 6,501,551 | B1 | 12/2002 | Tearney et al. |
| 6,564,087 | B1 | 5/2003 | Pitris et al. |
| 6,891,984 | B2 | 5/2005 | Petersen et al. |
| 7,061,618 | B2 | 6/2006 | Atia et al. |
| 7,530,948 | B2 | 5/2009 | Seibel et al. |
| 7,843,572 | B2 | 11/2010 | Tearney et al. |
| 7,864,822 | B2 | 1/2011 | Bouma et al. |
| 7,916,387 | B2 | 3/2011 | Schmitt |
| 8,078,245 | B2 | 12/2011 | Daly et al. |
| 8,384,909 | B2 | 2/2013 | Yun et al. |
| 8,416,818 | B2 | 4/2013 | Bouma et al. |
| 8,437,007 | B2 | 5/2013 | Flanders |
| 8,515,221 | B2 | 8/2013 | Flanders et al. |
| 8,531,655 | B2 | 9/2013 | Klein et al. |
| 8,711,364 | B2 | 4/2014 | Brennan et al. |
| 8,854,629 | B2 | 10/2014 | Frisken et al. |
| 8,868,356 | B2 | 10/2014 | Liu |
| 8,947,648 | B2 | 2/2015 | Swanson et al. |
| 8,994,954 | B2 | 3/2015 | Atia et al. |
| 9,008,142 | B2 | 4/2015 | Minneman et al. |
| 9,162,404 | B2 | 10/2015 | Doerr |
| 9,400,169 | B2 | 7/2016 | Zhou |
| 9,464,883 | B2 | 10/2016 | Swanson et al. |
| 9,683,928 | B2 | 6/2017 | Swanson |
| 10,107,616 | B2 | 10/2018 | Zhou |
| 10,126,572 | B2 | 11/2018 | Zhang et al. |
| 10,132,610 | B2 | 11/2018 | Swanson et al. |
| 10,191,145 | B2 | 1/2019 | Swanson |
| 10,401,883 | B2 | 9/2019 | Swanson et al. |
| 10,416,288 | B2 | 9/2019 | Swanson |
| 10,895,525 | B2 | 1/2021 | Swanson |
| 10,907,951 | B2 | 2/2021 | Avci |
| 10,969,571 | B2 | 4/2021 | Swanson |
| 11,256,080 | B2 | 2/2022 | Swanson |
| 2009/0074428 | A1* | 3/2009 | Liu .................... H04B 10/2513 398/208 |
| 2011/0218404 | A1 | 9/2011 | Hirakawa |
| 2011/0310378 | A1* | 12/2011 | Froggatt .............. G01D 5/3538 356/477 |
| 2012/0002971 | A1 | 1/2012 | Doerr |
| 2012/0099112 | A1* | 4/2012 | Alphonse ........... G01B 9/02044 385/12 |
| 2012/0226118 | A1* | 9/2012 | Delbeke ............... A61B 5/0031 600/316 |
| 2013/0044974 | A1 | 2/2013 | Doerr |
| 2014/0126990 | A1 | 5/2014 | Manes et al. |
| 2014/0147079 | A1 | 5/2014 | Doerr et al. |
| 2014/0160488 | A1* | 6/2014 | Zhou .................... A61B 5/0066 356/479 |
| 2014/0376000 | A1 | 12/2014 | Swanson et al. |
| 2016/0231101 | A1 | 8/2016 | Swanson |
| 2016/0357007 | A1 | 12/2016 | Swanson |
| 2017/0143196 | A1 | 5/2017 | Liang et al. |
| 2017/0205253 | A1 | 7/2017 | Handerek |
| 2020/0110258 | A1 | 4/2020 | Swanson |
| 2021/0149101 | A1 | 5/2021 | Swanson |

FOREIGN PATENT DOCUMENTS

| | | |
|---|---|---|
| EP | 1 839 375 B1 | 6/2014 |
| WO | 2014/088650 A1 | 6/2014 |
| WO | 2014/089504 A1 | 6/2014 |

OTHER PUBLICATIONS

Ralston, T.S., et al., "Interferometric synthetic aperture microscopy", Nature Physics, vol. 3, No. 2, 2007, pp. 129-134.

Rasras, M.S., et al., "Integrated resonance-enhanced variable optical delay lines", IEEE Photonics Technology Letters, vol. 17, No. 4, Apr. 4, 2005, pp. 834-836.

Roelkens, G., et al., "Grating Based Optical Fiber Interfaces for Silicon-On-Insulator Photonic Integrated Circuits", IEEE Journal of Selected Topics in Quantum Electronics, vol. 17, No. 3, May/Jun. 2011, pp. 571-580.

Rossant, F., et al., "Highlighting Directional Reflectance Properties of Retinal Substructures From D-OCT Images", IEEE Transactions on Biomedical Engineering, vol. 66, No. 11, Feb. 19, 2019, pp. 3105-3118.

Ryf, R., et al., "Photonic-Lantern-Based Mode Multiplexers for Few-Mode-Fiber Transmission", Proceedings of the Optical Fiber Communications Conference, Paper W4J.2., 2015, pp. 3.

Ryu, S.Y., et al., "Combined system of optical coherence tomography and fluorescence spectroscopy based on Double-cladding fiber", Optics Letters, vol. 33, No. 20, Oct. 15, 2008, pp. 2347-2349.

Alam, S. U., et al., "Recent Progress in the Development of Few Mode Fiber Amplifiers", Proceedings of the Optical Fiber Communications Conference, Paper Tu3C.1, 2015, pp. 3.

Sancho-Durá, J., et al., "Handheld multi-modal imaging for point-of-care skin diagnosis based on akinetic Integrated optics optical coherence tomography", Journal of Biophotonics, Jul. 10, 2018, 6 pages.

Sarunic, M., et al., "Instantaneous complex conjugate resolved spectral domain and swept-source OCT using 3×3 fiber couplers", Opt. Express, vol. 13, No. 3, 2005, pp. 957-967.

Sarunic, M.V., et al., "Real-Time Quadrature Projection Complex Conjugate Resolved Fourier Domain Optical Coherence Tomography", Optics Letters, vol. 31, No. 16, Aug. 15, 2006, pp. 2426-2428.

Schneider, S., et al., "Optical coherence tomography system mass-producible on a silicon photonic chip", Optics Express, vol. 24, No. 2, Jan. 2016, pp. 1573-1586.

Selvaraja, S.K., et al., "Record low-loss hybrid rib/wire waveguides for silicon photonic circuits", Group IV Photonics, 2010, pp. 3.

Siddiqui, M., et al., "Compensation of spectral and RF errors in swept-source OCT for high extinction complex demodulation", Opt. Express, vol. 23, No. 5, 2015, pp. 5508-5520.

Siddiqui, M., et al., "High-speed optical coherence tomography by circular interferometric ranging", Nature Photonics, vol. 12, 2018, pp. 111-116.

Sokolovskii, G.S., et al., "Bessel beams from semiconductor light sources", Progress in Quantum Electronics, vol. 38, No. 4, Jul. 2014, pp. 157-188.

Soref, R., "Tutorial: Integrated-photonic switching structures", APL Photonics, vol. 3, No. 2, Jan. 29, 2018, 19 pages.

Steinvurzel, P., et al., "Fiber-based Bessel beams with controllable diffraction-resistant distance", Optics Letters, vol. 36, No. 23, 2011, pp. 4671-4673.

(56) References Cited

OTHER PUBLICATIONS

Sun, J., et al., "Large-scale nanophotonic phased array", Nature, vol. 493, Jan. 9, 2013, pp. 195-199.
Sun, J., et al., "Large-Scale Silicon Photonic Circuits for Optical Phased Arrays", IEEE Journal of Selected Topics in Quantum electronics, vol. 20, No. 4, Jul./Aug. 2014, pp. 15.
Sun, J., et al., "Two-dimensional apodized silicon photonic phased arrays", Optics Letters, vol. 39, No. 2, Jan. 15, 2014, pp. 367-370.
Taillaert, D., et al., "A compact two-dimensional grating coupler used as a polarization splitter", IEEE Photonics Technology Letters, vol. 15, No. 9, 2003, pp. 1249-1251.
Takiguchi, K., et al., "Integrated-optic variable delay line and its application to a low-coherence reflectometer", Optics Letters, vol. 30, No. 2, Oct. 15, 2005, pp. 2739-2741.
Tearney, G.J., et al., "Spectrally encoded confocal microscopy", Optics Letters, vol. 23, No. 15, Aug. 1, 1998, pp. 1152-1154.
Tsai, T.-H., et al., "Ultrahigh speed endoscopic optical coherence tomography using micromotor imaging catheter and VCSEL technology", Biomed. Opt. Express, vol. 4, No. 7, 2013, pp. 1119-1132.
Tu, X., et al., "State of the Art and Perspectives on Silicon Photonic Switches", Micromachines, vol. 10, No. 51, 2019, 19 pages.
Vakoc, B., et al., "Phase-resolved optical frequency domain imaging", Optics Express, vol. 13, No. 14, 2005, pp. 5483-5493.
Vakoc, B.J., et al., "Elimination of depth degeneracy in optical frequency-domain imaging through polarization-based optical demodulation", Opt. Lett., vol. 31, No. 3, 2006, pp. 362-364.
Velazquez-Benitez, A.M., et al., "Six mode selective fiber optic spatial multiplexer", optics Letters, vol. 40, No. 8, Apr. 15, 2015, pp. 1663-1666.
Velha, P., et al., "Wide-band polarization controller for Si photonic integrated circuits", Optics Letters, vol. 41, No. 24, Dec. 15, 2016, pp. 5656-5659.
Vermeulen, D., et al., "High-efficiency fiber-to-chip grating couplers realized using an advanced CMOS-compatible silicon-on-insulator platform", Opt. Express, vol. 18, No. 17, 2010, pp. 18278-18283.
Vermeulen, D., et al., "Silicon-on-insulator polarization rotator based on a symmetry breaking silicon overlay", IEEE Photonics Technology Letters, vol. 24, No. 5, 2012, pp. 482-484.
Wang, R.K., "In vivo full range complex Fourier domain optical coherence tomography", Applied Physics Letters, vol. 90, No. 5, 54103, 2007, pp. 4.
Wang, R.K., et al., "Three dimensional optical angiography", Optics Express, vol. 15, No. 7, 2007, pp. 4083-4097.
Wang, X., and Mookherjea, S., "Compact high-extinction-ratio silicon photonic variable optical attenuators (VOAs)", Conference on Lasers and Electro-Optics, OSA Technical Digest (online) (Optica Publishing Group), 2017, paper SW1N.7, pp. 2.
Wang, X., et al., "Phase error corrected 4-bit true time delay module using a cascaded 2×2 polymer waveguide switch array", Applied Optics, vol. 46, No. 3, 2007, pp. 379-383.
Wang, Z., et al., "Depth-encoded all-fiber swept source polarization sensitive OCT", Biomed. Opt. Express, vol. 5, No. 9, 2014, pp. 2931-2949.
Weber, N., et al., "Highly compact imaging using Bessel beams generated by ultraminiaturized multi-micro-axicon systems", Journal of Optical Society of America A. vol. 29, No. 5, May 2012, pp. 808-816.
Wieser, W., et al., "High definition live 3D-OCT in vivo: design and evaluation of a 4D OCT engine with 1 GVoxel/s", Biomedical Optics Express, vol. 5, No. 9, 2014, pp. 2963-2977.
Wojtkowski, M., et al., "Full range complex spectral optical coherence tomography technique in eye imaging", Optics Letters, vol. 27, No. 16, 2002, pp. 1415-1417.
Wojtkowski, M., et al., "Ultrahigh-resolution, high-speed, Fourier domain optical coherence tomography and methods for dispersion compensation", Optics Express, vol. 12, No. 11, 2004, pp. 2404-2422.
Wörhoff, K., et al., "Design and application of compact and highly tolerant polarization-independent waveguides", IEEE J. Lightw. Technol., vol. 25, No. 5, May 2007, pp. 1276-1282.

Worhoff, K., et al., "Silicon Oxynitride Technology for Integrated Optical Solutions in Biomedical Applications", In: 13th International Conference on Transparent Optical Networks 2011, Jun. 26-30, 2011, Stockholm, Sweden, pp. 14.
Xi, J., "Generic real-time uniform K-space sampling method for high-speed swept-Source optical coherence tomography", Optics Express, vol. 18, No. 9, 2010, pp. 9511-9517.
Xie, J., et al., "Seven-bit reconfigurable optical true time delay line based on silicon integration", Optics Express, vol. 22, No. 19, 2014, pp. 22707-22715.
Xie, T., et al., "Fiber-Optic-bundle-based optical coherence tomography", Optics Letters, vol. 30, No. 14, Jul. 15, 2005, pp. 1803-1805.
Xie, Z., et al., "Axicon on a gradient index lens (AXIGRIN): integrated optical bench for Bessel beam generation from a point-like source", Applied Optics, vol. 53, Issue 26, 2014, pp. 6103-6107.
Yaacobi, A., et al., "Vertical emitting aperture nanoantennas", Optics Letters, vol. 37, No. 9, May 1, 2012, pp. 1454-1456.
Yamanari, M., et al., "Full-range polarization-sensitive swept-source optical coherence tomography by simultaneous transversal and spectral modulation", Opt. Express, vol. 18, No. 13, 2010, pp. 13964-13980.
Yazdanfar, S., et al., "High resolution imaging of in vivo cardiac dynamics using color Doppler optical coherence tomography", Optics Express, vol. 1, No. 13, 1997, pp. 424-431.
Acoleyen, K.V., et al., "Two-dimensional optical phased array antenna on silicon-on-insulator", Optics Express, vol. 18, No. 13, Jun. 21, 2010, pp. 13655-13660.
Aflatouni, F., et al., "Nanophotonic coherent imager", Optics Express, vol. 23, No. 4, 2015, pp. 5117-5125.
Akca, B.I., "Spectral-Domain Optical Coherence Tomography on a Silicon Chip", PhD Thesis. University of Twente, Paper 12424-50, 2012, pp. 164.
Akca, B.I., "Non-moving scanner design for OCT systems", Optics Express, vol. 24, No. 25, Dec. 12, 2016, pp. 28459-28466.
Akca, B.I., et al., "Miniature spectrometer and beam splitter for an optical coherence tomography on a silicon chip", Optics Express, vol. 21, No. 14, Jul. 3, 2014, pp. 16648-16656.
Akca, B.I., et al., "Toward Spectral-Domain Optical Coherence Tomography on a Chip", IEEE Journal of Selected Topics in Quantum Electronics, vol. 18, No. 3, 2012, pp. 1223-1233.
Almeida, V.R., et al., "Nanotaper for compact mode conversion", Optics Letters, vol. 28, No. 15, Aug. 1, 2003, pp. 1302-1304.
Baumann, B., et al., "Swept source / Fourier domain polarization sensitive optical coherence tomography with a passive polarization delay unit", Opt. Express, vol. 20, No. 9, 2012, pp. 10229-10241.
Biedermann, B.R., et al., "Dispersion, coherence and noise of Fourier domain mode locked lasers", Optics Express, vol. 17, No. 12, 2009, pp. 9947-9961.
Blatter, C., et al., "High-speed functional OCT with self-reconstructive Bessel illumination at 1300nm", Proceedings of the SPIE, paper 809104, Jun. 1, 2011, pp. 6.
Boer, J. F. De, and Milner, T.E., "Review of polarization sensitive optical coherence tomography and Stokes vector determination", J. Biomed. Opt., No. 7, No. 3, 2002, pp. 359-371.
Boer, J.F., et al., "Improved signal-to-noise ratio in spectral-domain compared with time-domain optical coherence tomography", Optics Letters, vol. 28, No. 21, 2003, pp. 2067-2069.
Boudoux, C., et al., "Rapid wavelength-swept spectrally encoded confocal microscopy", Optics Express, vol. 13, No. 20, 2005, pp. 8214-8221.
Bozinovic, N., et al., "Terabit-Scale Orbital Angular Momentum Mode Division Multiplexing in Fibers", Science Magazine, vol. 340, Issue 6140, Jun. 28, 2013, pp. 1545-1548.
Bru. L.A., et al., "Integrated optical frequency domain reflectometry device for characterization of complex integrated devices", Optics Express, vol. 26, No. 23, 2018, pp. 30000-30008.
Brzobohaty, O., et al., "High quality quasi-Bessel beam generated by round-tip axicon", Optics Express, vol. 16, No. 17, 2008, pp. 12688-12700.
Burns, J.A., et al., "A Wafer-Scale 3-D Circuit Integration Technology", IEEE Transactions on Electronic Devices, vol. 53, No. 10, Oct. 2006, pp. 2507-2516.

(56) References Cited

OTHER PUBLICATIONS

Chandrasekhar, S., and Liu, X., "Enabling Components for Future High-Speed Coherent Communication Systems", Optical Fiber Communication Conference Tutorial, 2011, pp. 5.
Chen, H., et al., "Compact spatial multiplexers for mode division multiplexing", Optics Express, vol. 22, No. 26, Dec. 26, 2014, pp. 31582-31594.
Chen, H., et al., "Design Constraints of Photonic-Lantern Spatial Multiplexer Based on Laser-Inscribed 3-D Waveguide Technology", Journal of Lightwave Technology, vol. 33, No. 6, Mar. 15, 2015, pp. 1147-1154.
Chen, L., et al., "Low-Loss and Broadband Cantilever couplers Between Standard Cleaved Fibers and High-Index-Contrast Si3N4 or Si Waveguides", IEEE Photonics Technology Letters, vol. 22, No. 23, Dec. 1, 2010, pp. 1744-1746.
Chen, L., et al., "Monolithically integrated 40-wavelength demultiplexer and photodetector array on silicon", IEEE Photonics Technology Letters, vol. 23, No. 13, 2011, pp. 869-871.
Chinn, S.R., et al., "Optical coherence tomography using a frequency-tunable optical source", Optics Letters, vol. 22, No. 5, 1997, pp. 340-342.
Choi, E., et al., "All-fiber variable optical delay line for applications in optical coherence tomography: feasibility study for a novel delay line", Optics Express, vol. 14, No. 4, Feb. 21, 2005, pp. 1334-1345.
Choma, M.A., et al., "Sensitivity advantage of swept source and Fourier domain optical Coherence tomography", Optics Express, vol. 11, No. 18, 2003, pp. 2183-2189.
Chu, T., et al., "Compact 1×N thermo-optic switches based on silicon photonic wire waveguides", Optics Express, vol. 13, No. 25, 2005, pp. 10109-10114.
Cui, D., et al., "Multifiber angular compounding optical coherence tomography for speckle reduction", Optics Letters, vol. 42, No. 1, 2107, pp. 125-128.
Culemann, D., et al., "Integrated optical sensor in glass for optical coherence tomography (OCT)", IEEE Sel. Topics Quantum Electron., vol. 6, No. 5, Oct. 2000, pp. 730-734.
Derose, C.T., et al. "Electronically controlled optical beam-steering by an active phased array of metallic nanoantennas", Optics Express, vol. 21, No. 4, Feb. 25, 2013, pp. 5198-5208.
Doerr, C., et al., "Single-chip silicon photonics 100-Gb/s coherent transceiver", in Optical Fiber Communication Conference, (Optical Society of America, 2014), paper Th5C.1, 2014, pp. 3.
Doerr, C.R., and Buhl, L.L., "Circular Grating Coupler for Creating Focused Azimuthally and Radially Polarized Beams," Optics Letters, vol. 36, No. 7, Apr. 1, 2011, pp. 1209-1211.
Doerr, C.R., and Chen, L., "Monolithic PDM-DQPSK receiver in silicon", IEEE 36th European Conference and Exhibition on Optical Communication, 2010, 3 pages.
Doylend, J.K., et al., "Two-dimensional free-space beam steering with an optical phased array on silicon-on-insulator", Optics Express, vol. 19, No. 22, Oct. 4, 2011, pp. 21595-21604.
Dupuis, N., et al., "InP-based comb generator for optical OFDM", Journal of Lightwave Technology, Optical Fiber Communication Conference, vol. 30, No. 4, 2011, pp. 466-472.
Fechtig, D.J., et al., "Line-field parallel swept source MHz OCT for structural and functional retinal imaging", Biomedical Optics Express, vol. 6, No. 3, 2105, pp. 716-735.
Fercher, A.F., et al., "Measurement of intraocular distances by backscattering spectral interferometry", Optics Communications, vol. 117, No. 1, 1995, pp. 43-48.
Fujimoto, J.G., et al., European Inventor Award 2017, PRWeb, Jun. 15, 2017, 3 pages.
Gourley, K., et al.. , "First experimental demonstration of a Fresnel Axicon," Proceedings of the SPIE, Jun. 18, 2008, pp. 7.
Hansuek, L., et al., "Ultra-low-loss optical delay line on a silicon chip", Nature Communications, vol. 3, Article No. 867, May 29, 2012, pp. 1-7.
Hee, M.R., et al., "Polarization-sensitive low-coherence reflectometer for birefringence characterization and ranging", Journal of the Optical Society of America B, vol. 9, No. No. 6, 1992, pp. 903-908.
Heismann, F., "Analysis of a Reset-Free Polarization Controller for Fast Automatic Polarization Stabilization in Fiber-optic Transmission Systems", Journal of Lightwave Technology, vol. 12, No. 4, 1994, pp. 690-699.
Hillmann, D., et al., "Common approach for compensation of axial motion artifacts in swept-source OCT and dispersion in Fourier-domain OCT", Optics Express, vol. 20, No. 6, 2012, pp. 6761-6776.
Hofer, B., et al., "Dispersion encoded full range frequency domain optical coherence tomography", Opt. Express, vol. 17, No. 1, 2009, pp. 7-24.
Huang, D., et al., "Optical coherence tomography", Science, vol. 254, No. 5035, 1991 , pp. 1178-1181.
Huang, Y., et al., "Wide-field high-speed space-division multiplexing optical coherence tomography using an Integrated photonic device", Biomedical Optics Express, vol. 8, No. 8, Aug. 1, 2017, pp. 3856-3867.
Yerolatsitis, S., et al., "Tapered Mode Multiplexers for Single Mode to Multi Mode Fibre Mode Transitions", Proceedings of the Optical Fiber Communications Conference, Paper w3B.4, 2015, pp. 3.
Yun, S. H., et al., "Removing the depth-degeneracy in optical frequency domain imaging with frequency shifting", Opt. Express, vol. 12, No. 20, 2004, pp. 4822-4828.
Yun, S., et al., "High-speed optical frequency-domain imaging", Optics Express, vol. 11, No. 22, 2003, pp. 2953-2963.
Yurtsever, G., et al., "Integrated photonic circuit in silicon on insulator for Fourier Domain optical coherence tomography," in Proc. SPIE, Opt. Coherence Tomography Coherence Domain Opt. Methods Biomed. XIV, vol. 7554, San Francisco, CA, 2010, pp. 1-5.
Yurtsever, G., et al., "Photonic integrated Mach-Zehnder interferometer with an on-chip reference arm for optical coherence tomography", Biomedical Optics Express, vol. 5, Issue 4, 2014, pp. 1050-1061.
Yurtsever, G., et al., "Ultra-compact silicon photonic integrated Interferometer for swept-source optical coherence tomography", Opt. Lett., vol. 39, No. 17, 2014, pp. 5228-5231.
Zaoui, W.S., et al., "Cost-effective CMOS-compatible grating couplers with backside metal mirror and 69% coupling efficiency", Optics Express, vol. 20, No. 26, Dec. 10, 2012, pp. B238-B243.
Zhou, C., et al., "Space-division multiplexing optical coherence tomography", Optics Express, Aug. 6, 2013, vol. 21, No. 16, p. 19219-19227.
Zhou, H., et al., "All-in-one silicon photonic polarization processor", Nanophotonics, vol. 8, No. 12, 2019, pp. 2257-2267.
Zhour, C., et al., "Space-division multiplexing optical coherence tomography", Optics Express, vol. 21, No. 16, 2013, pp. 19219-19227.
Zhuang, L., et al., "Low-loss, high-index-contrast Si3N4/SiO2 optical waveguides for optical delay lines in microwave photonics signal processing", Optics Express, vol. 19, No. 23, 2011, pp. 23162-23170.
Restriction Requirement dated Jun. 4, 2018 in U.S. Appl. No. 15/147,775, 7 pages.
Non-Final Office Action dated Aug. 27, 2018 in U.S. Appl. No. 15/147,775, 9 pages.
Final Office Action dated Mar. 8, 2019 in U.S. Appl. No. 15/147,775, 9 pages.
Non-Final office Action dated Sep. 3, 2020 in U.S. Appl. No. 16/704,851, 12 pages.
Final Office Action dated Mar. 31, 2021 in U.S. Appl. No. 16/704,851, 12 pages.
Notice of Allowance dated Oct. 4, 2021 in U.S. Appl. No. 16/704,851, 5 pages.
Huber, R., et al., "Buffered Fourier domain mode locking: unidirectional swept laser sources for optical coherence tomography imaging at 370,000 lines/s", Optics Letters, vol. 31, No. 20, 2006, pp. 2975-2977.
Huber, R., et al., "Fourier Domain Mode Locking (FDML): A new laser operating regime and applications for optical coherence tomography", Optics Express, vol. 14, No. 8, 2006, pp. 3225-3237.
Huber, R., et al., "Amplified, frequency swept lasers for frequency domain reflectometry and OCT imaging: design and scaling principles", Optics Express, vol. 13, No. 9, 2005, pp. 3513-3528.

(56) References Cited

OTHER PUBLICATIONS

Huber, R., et al., "Three-dimensional and C-mode OCT imaging with a compact, frequency swept laser source at 1300 nm", Optics Express, vol. 13, No. 26, 2005, pp. 10523-10538.

Izutsu, M., et al., "Integrated optical SSB modulator/frequency shifter", IEEE Journal of Quantum Electronics, vol. 17, No. 11, 1981, pp. 2225-2227.

Jayaraman, V., et al., "High-sweep-rate 1310 nm MEMS-VCSEL with 150 nm continuous tuning range", Electron. Lett., vol. 48, No. 14, 2012, pp. 867-869.

Jayaraman, V., et al., "Rapidly swept, ultra-widely-tunable 1060 nm MEMS-VCSELs", Electronics Letters, vol. 48, No. 21, Oct. 11, 2012, pp. 1331-1333.

Ji, X., et al., "On-chip tunable photonic delay line", APL Photonics, vol. 4, 2019, pp. 090803-1-090803-7.

Jia, Y., et al., "Split-spectrum amplitude-decorrelation angiography with optical coherence tomography", Opt. Express, vol. 20, No. 4, 2012, pp. 4710-4725.

Jinguji, K., et al., "Two-port optical wavelength circuits composed of cascaded Mach-Zehnder interferometers with point-symmetrical configurations", IEEE, Journal of Lightwave Technology, vol. 14, No. 10, 1996, pp. 2301-2310.

Khilo, A., et al., "Efficient planar fiber-to-chip coupler based on two-stage adiabatic evolution", Optics Express, vol. 18, No. 15, Jul. 19, 2010, pp. 15790-15806.

Koch, B., et al., "Versatile endless optical polarization controller/tracker/demultiplexer", Optics Express, vol. 22, No. 7, 2014, pp. 8259-8276.

Lee, B.G., and Dupuis, N., "Silicon Photonic Switch Fabrics: Technology and Architecture", Journal of Lightwave Technology, vol. 37, No. 1, Oct. 18, 2018, 15 pages.

Lee, Kye-Sung., et al., "Dual detection full range frequency domain optical coherence tomography", Opt. Lett., vol. 35, No. 7, 2010, pp. 1058-1060.

Leitgeb, R., et al., "Performance of fourier domain vs. time domain optical coherence tomography", Optics Express, vol. 11, No. 8, 2003, pp. 889-894.

Lemire-Renaud, S., et al., "Double-clad fiber coupler for endoscopy", Optics Express, vol. 18, No. 10, Apr. 26, 2010, pp. 9755-9764.

Leon-Saval, S.G., et al., "Mode-selective photonic lanterns for space-division multiplexing", Optics Express, vol. 22, No. 1, Jan. 13, 2014, pp. 9.

Liang, K., et al., "Cycloid Scanning for Wide Field Optical Coherence Tomography Endomicroscopy and angiography in Vivo", Optica, vol. 5, No. 1, 2018, pp. 36-43.

Lippok, N., et al., "Dispersion compensation in Fourier domain optical coherence tomography using the fractional Fourier transform", Optics Express, vol. 20, No. 21, 2012, pp. 23398-23413.

Liu, A., et al., "High-speed optical modulation based on carrier depletion in a silicon waveguide", Optics Express vol. 15, No. 2, 2007, pp. 660-668.

Liu, A.Y., et al., "High performance continuous wave 1.3 μm quantum dot lasers on silicon", Applied Physics Letters, vol. 104, 041104, 2014, pp. 4.

Lorenser, D., et al., "Energy-efficient low-Fresnel-number Bessel beams and their application in optical coherence tomography", Optics Letters, vol. 39, No. 3, Feb. 1, 2014, pp. 548-551.

Lu, C.D., et al., "Handheld ultrahigh speed swept source optical Coherence tomography instrument using a MEMs scanning mirror", Biomedical Optics Express, vol. 5, No. 1, 2014, pp. 293-311.

Mack, J.P., et al., "Photonic integrated circuit switch matrix and waveguide delay lines for optical packet synchronization", IEEE, 34th European Conference on Optical Communication, vol. 4, 2008, pp. 87-88.

Makita, S., et al., "Optical coherence angiography", Optics Express, vol. 14, No. 17, 2006, pp. 7821-7840.

Margallo-Balbás, E., et al., "Miniature Optical Coherence Tomography System Based on Silicon Photonics", SPIE BiOS, Proceedings, vol. 6847, 2008, pp. 11.

Margallo-Balbás, E., et al., "Miniature 10 kHz thermo-optic delay line in silicon", Optics Letters, vol. 35, No. 23, Dec. 2010, pp. 4027-4029.

Mekis, A., et al., "A Grating-Coupler-Enabled CMOS Photonics Platform", IEEE Journal of Selected epics in Quantum Electronics, vol. 17, Issue 3, May/Jun. 2011, pp. 597-608.

Mekis, A., et al., "Two-dimensional photonic crystal couplers for unidirectional light output", Optics Letters, vol. 25, No. 13, 2000, pp. 942-944.

Merola, F., et al., "Fabrication and test of polymeric microaxicons", Proceedings of the SPIE, vol. 8428, Jun. 1, 1012, pp. 12.

Morgner, U., et al., "Spectroscopic optical coherence tomography", Optics Letters, vol. 25, No. 2, 2000, pp. 111-113.

Na, N., et al., "Efficient broadband silicon-on-insulator grating coupler with low backreflection", Optics Letters, vol. 36, No. 11, Jun. 1, 2011, pp. 2101-2103.

Nadkarni, S.K., et al., "Measurement of Collagen and Smooth Muscle Cell Content in Atherosclerotic Plaques Using Polarization-Sensitive Optical Coherence Tomography", J. Am. Coll. Cardiol., vol. 49, No. 13, 2007, pp. 1474-1481.

Nagarajan, R., et al., "10 Channel, 100Gbit/s per Channel, Dual Polarization, Coherent QPSK, Monolithic InP Receiver Photonic Integrated Circuit", Optical Fiber Communication Conference Proceedings, paper OML7, 2011, pp. 3.

Neill, D., et al., "Compact polarization diverse receiver for biomedical imaging Applications", SPIE Proceedings, vol. 7891, Jan. 22, 2011, pp. 5.

Nguyen, V.D., et al., "SiON integrated optics elliptic couplers for Fizeau-based optical coherence tomography," IEEE J. Lightw. Technol., vol. 28, No. 19, Sep. 2010, pp. 2836-2842.

Nguyen, V.D., et al., "Integrated-optics-based swept-source optical coherence tomography", Optics Letters, vol. 37, No. 23, Dec. 1, 2012, pp. 4820-4822.

Nguyen, V.D., et al., "Spectral domain optical coherence tomography imaging with an integrated optics spectrometer", Optics Letters, vol. 36, No. 7, Apr. 1, 2011, pp. 1293-1295.

Nitkowski, A., et al., "Nanophotonic Spectrometer for Optical Coherence Tomography", Imaging and Applied Optics Conference, OSA Technical Digest, Paper AM1B.3, 2013, pp. 3.

Noé, R., et al., "Automatic endless polarization control with integrated-optical Ti:LiNbO3 polarization transformers", Optics Letters, vol. 13, No. 6, 1988, pp. 527-529.

Noe, R., et al., "Endless Polarization Control Systems for Coherent Optics", Journal of Lightwave Technology, vol. 6, No. 7, INSPEC Accession No. 3251123, 1988, pp. 1199-1208.

Oduro, O., et al., "Selective Excitation of High Order Modes in Few Mode Fibres Using Optical Microfibres," Proceedings of the Optical Fiber Communications Conference, Paper M3D.5, 2015, pp. 5.

Omran, H., et al., "Deeply-Etched Optical MEMS Tunable Filter for Swept Laser Source Applications", IEEE Photonics Technology Letters. vol. 6, No. 1, Jan. 2014, pp. 37-39.

Pahlevaninezhad, H. et al., "Fiber-Based Polarization Diversity Detection for Polarization-Sensitive Optical Coherence Tomography", Photonics, vol. 1, No. 4, 2014, pp. 283-295.

Park, B.H., et al., "Jones matrix analysis for a polarization-sensitive optical coherence tomography system using fiber-optic components", Optics Letters, vol. 29, No. 21, 2004, pp. 2512-2514.

Park, G.C., et al., "Hybrid III-V/SOI Vertical Cavity Laser with In-plane Output into a Si Waveguide", Paper W2A.17, Proceedings of the Optical Fiber communication Conference, 2015, pp. 2.

Pircher, M., et al., "Polarization sensitive optical coherence tomography in the human eye", Prog. Retin. Eye. Res., vol. 30, No. 6, 2011, pp. 431-451.

Potsaid, B., et al., "MEMS tunable VCSEL light source for ultrahigh speed 60kHz-1 MHz axial scan rate and long range centimeter class OCT imaging", in SPIE BiOS, International Society for Optics and Photonics, 2012, pp. 9.

Potsaid, B., et al., "Ultrahigh speed spectral / Fourier domain OCT ophthalmic imaging at 70,000 to 312,500 axial scans per second", Optics Express, vol. 16, No. 19, 2008, pp. 15149-15169.

(56) References Cited

OTHER PUBLICATIONS

Preston, K., et al., "OCTANE: Optical Coherence Tomography Advanced Nanophotonic Engine", CLEO 2013, OSA Technical Digest, Paper AW3I.5, Jun. 9-14, 2013, 12 pages.

* cited by examiner

-Prior Art-

-Prior Art-

-Prior Art-

-Prior Art-

OPTICAL INSTRUMENT FOR IMAGING AND SENSING USING MULTICORE FIBER

RELATED APPLICATION SECTION Related Application Section

The present application is a continuation of U.S. patent application Ser. No. 16/704,851, entitled "Fixed Distal Optics Endoscope Employing Multicore Fiber", filed on Dec. 5, 2019, which is a divisional application of U.S. patent application Ser. No. 15/147,775, entitled "Fixed Distal Optics Endoscope Employing Multicore Fiber", filed on May 5, 2016, which claims priority to U.S. Provisional Application Nos. 62/166,154 filed on May 26, 2015, 62/163,522 filed on May 19, 2015, 62/163,532 filed on May 19, 2015, and 62/157,131 filed on May 5, 2015. The entire contents of U.S. patent application Ser. Nos. 15/147,775, and 16/704,851 and U.S. Provisional Application Nos. 62/166,154, 62/163,522, 62/163,532, and 62/157,131 are herein incorporated by reference.

TECHNICAL FIELD

This disclosure relates generally to endoscopic devices and in particular to a fixed distal optics endoscope having multicore fiber.

BACKGROUND

Medical and non-medical applications of imaging endoscopes are well known and their importance to contemporary cardiology, gastroenterology, pulmonology, laparoscopy as well as nondestructive evaluation/nondestructive testing (NDE/NDT) is widely accepted. Given that importance, improvements to endoscopic devices and systems would represent a welcome addition to the art.

SUMMARY

An advance in the art is made according to an aspect of the present disclosure directed to endoscopic devices employing multicore optical fiber.

In contrast to contemporary, prior-art endoscopic devices and systems, devices constructed according to the present disclosure may employ—in addition to multicore optical fiber—employ a variety of measurement techniques including swept-source techniques, employ widely tunable source(s), include multiple functions, and—in some embodiments—critical complex optical functions may be performed by one or more photonic integrated circuit(s).

An illustrative endoscopic system and structure according to the present disclosure includes an optical receiver selected from the group consisting of spectral domain optical coherence tomography (OCT) receiver, time domain OCT receiver, confocal receiver, fluorescence receiver, and Raman receiver; an endoscope body including fixed distal optics; and a multicore optical fiber optically coupling the fixed distal optics to the receiver.

Notably, term endoscope is used throughout the disclosure to describe structures according to the present disclosure. Those skilled in the art will readily appreciate that the disclosure is not specifically limited to endoscopes. More particularly, the disclosure and underlying principles herein are equally applicable to catheters, laparoscopes, imaging guidewires as well as other medical and non-medical devices and structures. Accordingly, when the term endoscope is used, it is intended that it be interchangeable with any instrument or system used to examine the inside of something—oftentimes a body for medical reasons. Such instruments advantageously permit the interior of an organ or other cavity of the body. Of further advantage, endoscopes are capable of being inserted directly into an organ for subsequent examination.

BRIEF DESCRIPTION OF THE DRAWING

A more complete understanding of the present disclosure may be realized by reference to the accompanying drawings in which:

FIG. 7(A) a collimating lens, FIG. 7(B) a fiber/lens coupling element including a passive or active beam steering elements, FIG. 7(C) a graduated index (GRIN) lens or section of multimode fiber, FIG. 7(D) a multi-element collimating lens, and FIG. 7(E) a beam deflector element according to aspects of the present disclosure;

DETAILED DESCRIPTION

Figure 1:
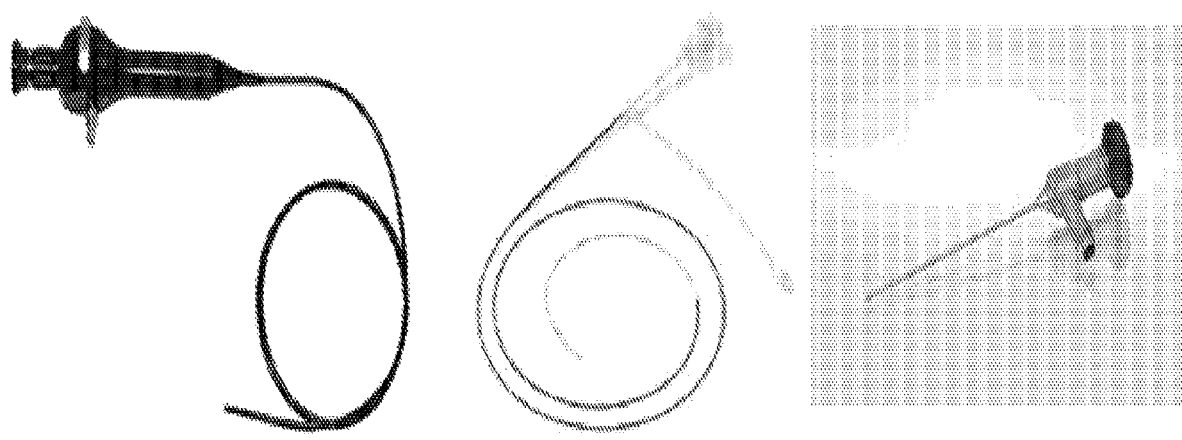
FIG. 1 shows exemplary Prior Art endoscopes.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

By way of some additional background, it is noted that many contemporary imaging endoscopes, catheters, laparoscopes, and imaging guidewires—such as those employed in optical coherence tomography systems—typically employ single mode optical fiber. Such systems perform scanning and imaging by either: 1) spinning the fiber or 2) employing distal optics—for example, motor(s) and actuator(s)—along with a stationary single mode optical fiber. As may be appreciated, configurations such as 1) and 2), above, provide necessary beam deflection(s) to effect the scanning.

Turning now to FIG. 1 there is shown several illustrations of contemporary optical endoscopes that are known in the art. While not specifically identified in that Figure, such endoscopes may include an eyepiece, a light post, and an objective assembly. Alternative configurations may include—among other things—an access port for instrument(s) and an "umbilical" connection.

Figure 2A:
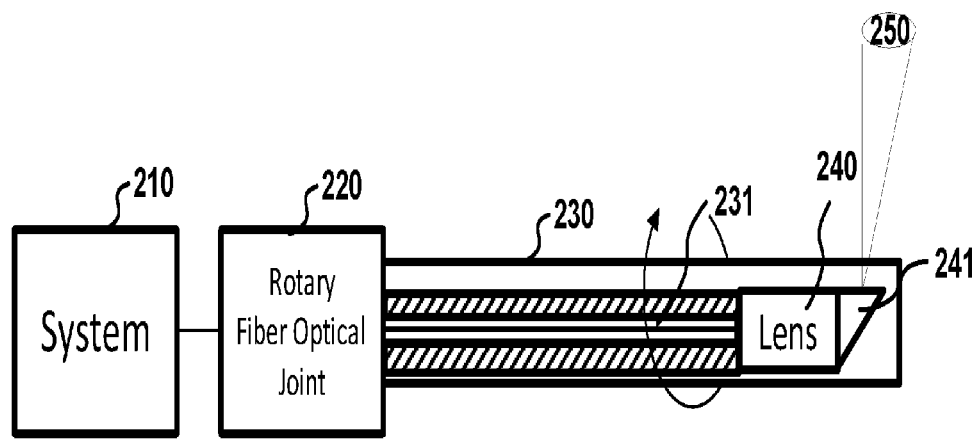
FIG. 2(A), FIG. 2(B) and FIG. 2(C) show a series of exemplary single-mode fiber scanning endoscopes as known in the Prior Art.
Figure 2B:
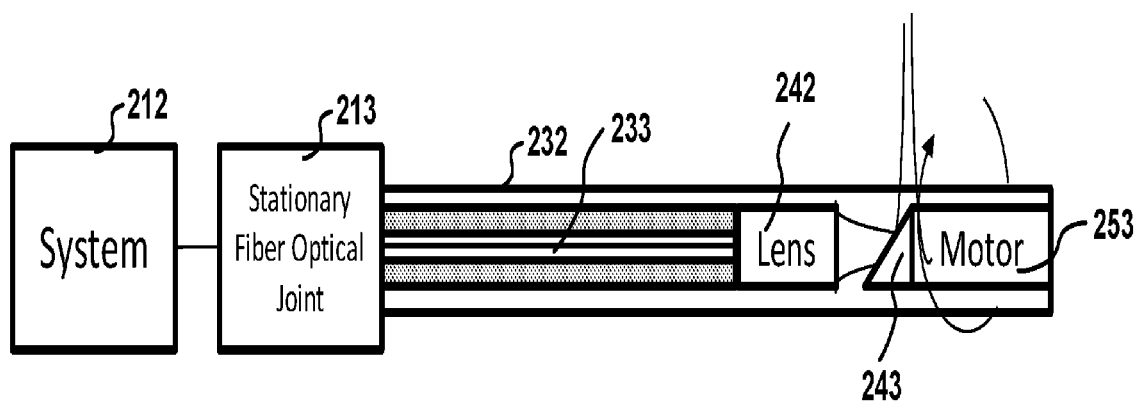
Figure 2C:
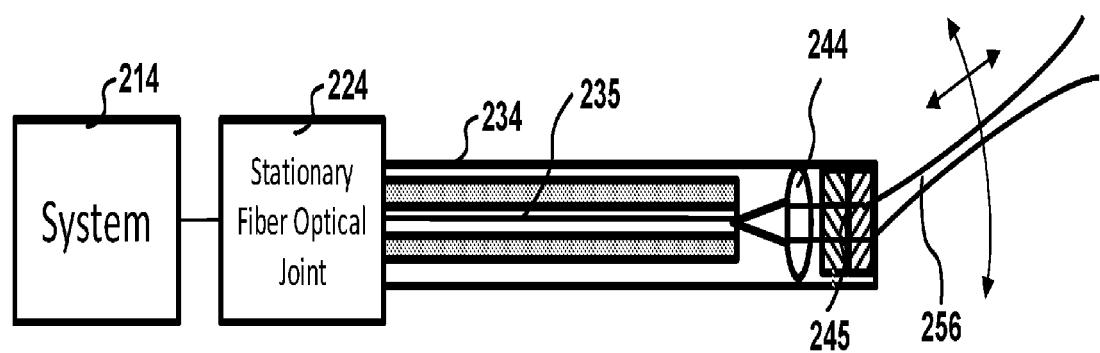

FIG. 2(A), FIG. 2(B) and FIG. 2(C) show in schematic form several illustrative examples of single-mode, or multi-mode fiber scanning endoscopes as known in the art. As may be appreciated such endoscopes must be capable of delivering, focusing, scanning and collecting a single spatial-mode optical beam. In addition, the catheter employed oftentimes is flexible—but not always—and has a sufficiently small diameter to facilitate its entry into internal spaces such as arteries. Generally, such endoscopes will include optical control and coupling element(s) at a proximal end, a single-mode fiber running the length of the catheter, and optical focusing and beam directing elements at the distal end. As is generally known by those skilled in the art, the endoscope is configured to scan the beam in a circumferential pattern such that a cross-section image may be made of structure(s) into which it is positioned such as—for example—an artery.

As shown in FIG. 2(A), such illustrative examples generally include—at a proximal end—a system 210 which may include light source(s), detector(s) and controlling circuitry and/or operating software(s). Such a system is optically, mechanically, and electrically coupled to a catheter body 230 by a rotary fiber optical joint 220 which includes a spinning optical fiber 231 which in turn is connected—at a distal end—to one or more lens(es) 240 and prism 241 which in turn produces a spatial mode optical beam 250.

The illustrative example shown in FIG. 2(B) includes—at its proximal end—system 212, stationary fiber optical joint 213 which is coupled to catheter body 232 and includes a fixed, or stationary, otherwise non spinning single mode optical fiber 233 which in turn is coupled—at the distal end—to one or more lens(es) 242 which in turn is optically coupled to a prism 243 which is spun by distal motor 253.

Similarly, the illustrative example shown in FIG. 2(C) includes system 214, stationary fiber optical joint 224, catheter body 234 including stationary single mode optical fiber 235 optically coupled at a distal end to lens(es) 244 and optical phased array(s) 245 thereby producing scanning beam 256.

As may be appreciated, spinning optical fibers—such as those employed in configurations such as that in FIG. 2(A), exhibit several disadvantages including non-uniform rotation distortion (NURD), fragility/breakage, cost, reliability, rotational speed limitations along with certain safety considerations that accompany such configurations. Distal motors—such as those employed in FIG. 2(B)—likewise are disadvantaged by cost, size, scanning flexibility, the need for control line(s) and power delivered to the distal end. Distal optical phased arrays—such as those employed in FIG. 2(C)—while offering optimistic promise nevertheless exhibit limitations with respect to image quality, efficiency sidelobes, electrical power requirements and size.

Given such noted infirmities with these prior art endoscopes, scanning optical endoscopes exhibiting low cost, small size and acceptable (albeit lower) scanning resolution may be may be constructed according to aspects of the present disclosure. More particularly, and with reference to FIG. 3, there is shown in schematic an illustrative multi-core fiber endoscope 300 according to an aspect of the present disclosure employing an array of swept-source optical coherence tomography (OCT) receivers. As shown in that figure, a multi-core optical fiber is employed and—in sharp contrast to the prior art—no distal mechanical element(s), controllable phased array(s), and/or spinning fibers are used. Of further advantage, individual optical fibers employed may be single-mode fiber(s) or multi-mode fiber(s). It is noted at this point that while specific illustrative examples disclosed herein employ SS-OCT systems and techniques—the disclosure is not so limited. More particularly, other OCT systems and non-OCT systems such as Raman, fluorescence, near-infrared, confocal, and other types of imaging systems that connect similar multicore fiber endoscopes with multi-core optical fiber are contemplated and within the scope of this disclosure as well.

A multi-core fiber (MCF) has multiple cores positioned within a cladding. Such MCF have been employed in telecommunications applications and shown considerable promise. Advantageously, the number of cores comprising a MCF may differ from application to application—as those individual application needs dictate. By way of illustrative example only—a seven core MCF may have one center and six outer cores. The distance between two neighboring cores is known as the core pitch. By altering the core pitch—it is known by those skilled in the art—that the amount of crosstalk between neighboring cores may be changed.

Figure 3:
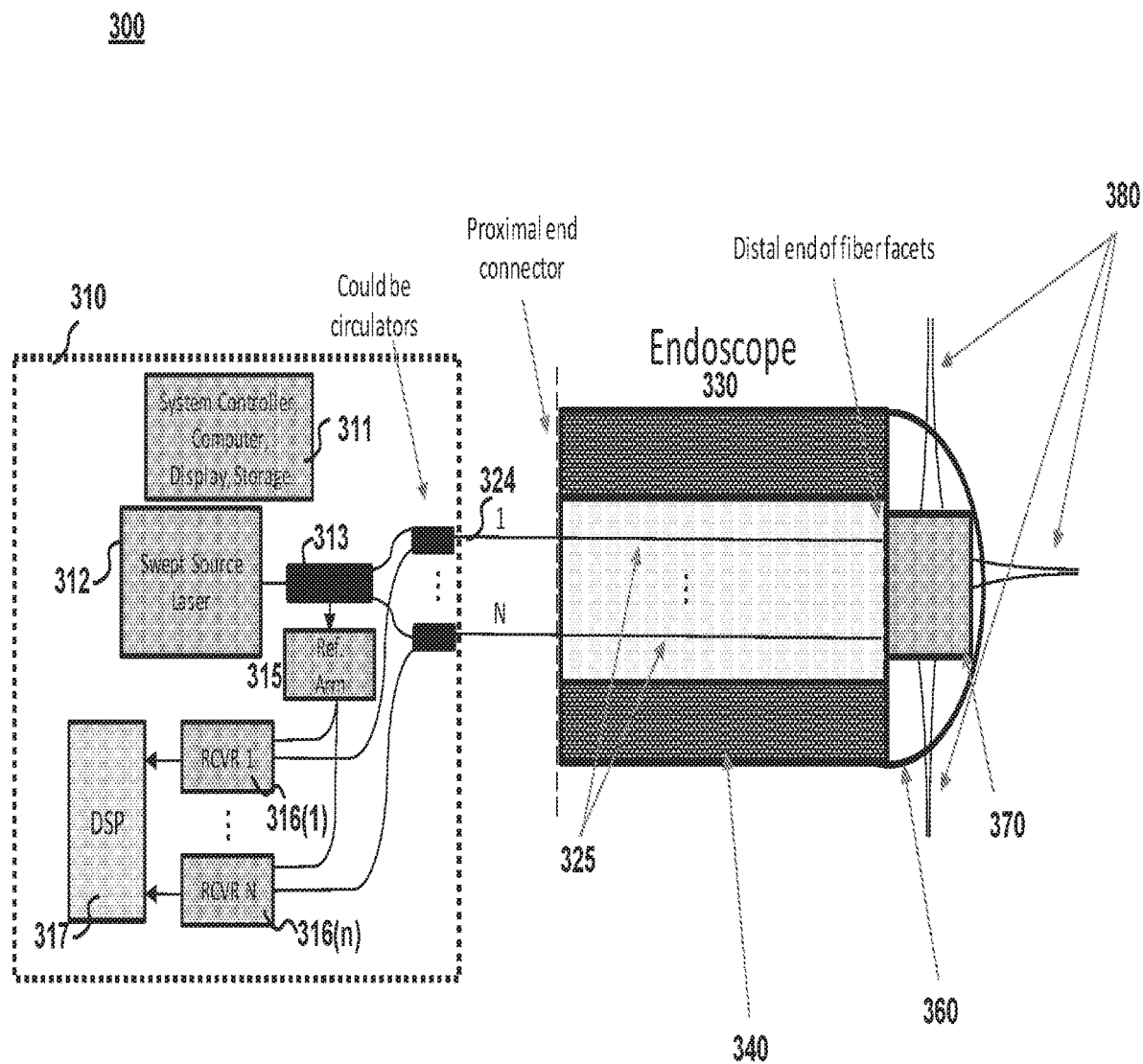
FIG. 3 shows a schematic diagram of a multi-core fiber endoscope employing an array of swept-source optical coherence tomography (SS-OCT) receivers according to an aspect of the present disclosure.

In the illustrative example shown in FIG. 3, a swept-source optical coherence tomography system 310 is coupled to a multi-core optical fiber endoscope 330. As previously noted either single-mode or multi-mode fibers may be employed however for SS-OCT systems such as the one illustrated single-mode fibers are preferably used. Additionally, and as previously noted, while we have shown illustratively an SS-OCT system in this Figure and described in this description, those skilled in the art will readily appreciate that any of a variety of measurement system(s) may be employed and remain consistent with one or more aspect(s) of the present disclosure.

As depicted in FIG. 3, a swept source laser 312 is split into N different channels through the effect of splitter 313 or other suitable optical structure(s), each of the N channels optically coupled to a multi-core optical fiber 324 via a proximal end connected (shown in Figure as a dotted line). The N channels are conveyed via the multi-core optical fiber to distal optical structure(s) 370 that may focus light through a transparent, protective cover 360—or transparent windows in a transparent cover—such that output light 380 is conveyed into any external sample, i.e., body tissue(s) or cavities.

As will be now understood, light reflected from the sample(s) is collected along the same optical path(s), combined with light directed to a reference arm 315 and interferometrically detected in N separate, opto-electronic receivers 316(1) . . . 316(n), the output of which is directed into a digital signal processing sub-system 317 and other computer(s), controller(s), instrumentation—as necessary (not specifically shown)—for analysis and/or display. Notably, an endoscope such as the one illustrated 330 may include a protective and/or structural jacket 340 to ensure integrity and/or smooth operation/insertion of the device as it is routed through other instruments or directly into a body lumen or other sample environment. Of further note that while this portion of the description has been directed to an SS-OCT type system those skilled in the art will appreciate that systems according to the present disclosure are not so limited. In particular, other types of optical sensing, ranging, or imaging modalities may be employed (e.g., fluorescence, Raman, near-infrared spectroscopy, etc.) in systems according to the present disclosure.

As may be further appreciated by those skilled in the art, the distal optical structures may advantageously include one or more passive lens assemblies or photonic integrated circuit(s) (PIC). Additionally, planar lightwave circuits (PLC) comprising those optical structures may advantageously be fabricated from InP or Si photonic materials—among others. By employing one or more PICs fabricated from well-known materials using highly evolved fabrication technologies contemporary design tools may be employed to design, simulate and manufacture the distal optical structures while producing benefits related to high precision, small size and low-cost. Still further, such distal optics according to the present disclosure may be fabricated—either in whole or in part—from molded optical materials and components thereby further lowering their cost and manufacturability.

Notably, while the distal optics of the system so described may comprise one or more PICs—so may elements of the SS-OCT portion 310 of the system. More particularly, on one illustrative embodiment according to the present disclosure—the SS-OCT portion of the system 310 shown schematically within the dotted line of FIG. 3, (excluding any elements/components not suitable for PIC fabrication presently—i.e., computers, etc.) may comprise one or more PICs such that a compact, robust, low-cost structure(s) result. As those skilled in the art will further appreciate and as will become apparent to those skilled in the art, such PIC fabrication methodologies may advantageously be applied to other designs/configurations according to the present disclosure including those described herein.

Of particular interest to those skilled in the art is that while employing a PIC a vertical cavity surface emitting laser (VCSEL) or other laser structure such as verner tuned laser may be integrated into an SS-OCT PIC such that a single PIC includes a VCSEL transmitter, waveguide(s) for beam handling and one or more optical receivers such as a dual-balanced, dual-polarization, I/Q receiver—among other(s). In sharp contrast to contemporary configurations, such PICs may be designed so that VCSEL emission light is coupled into a silicon waveguide.

Figure 4:
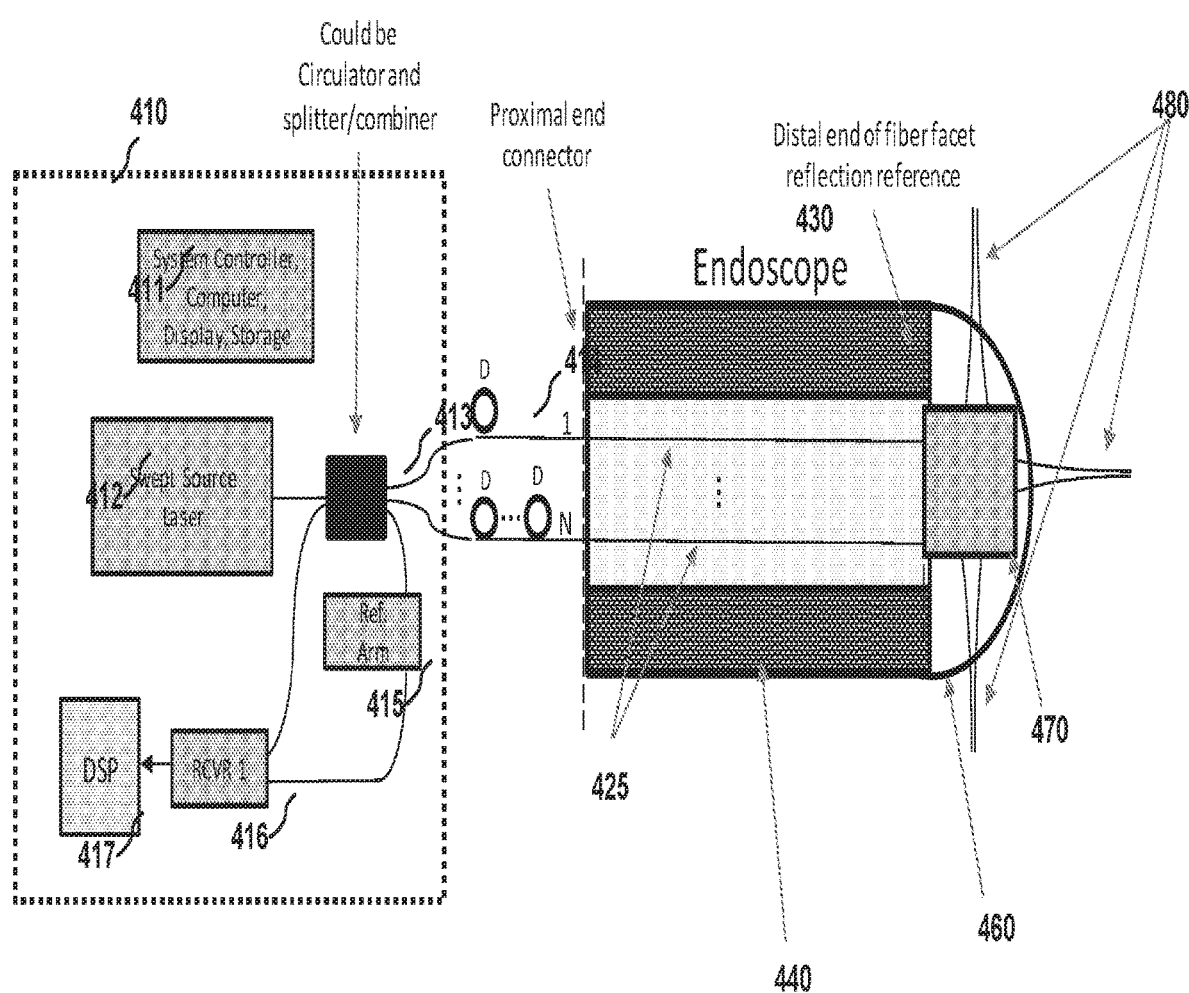
FIG. 4 shows a schematic diagram of a multi-core fiber endoscope employing a single SS-OCT receiver and distinct delays according to an aspect of the present disclosure.

With reference now to FIG. 4, there is shown a schematic of an illustrative embodiment of a multi-core fiber endoscope system 400 employing a single SS-OCT receiver and distinct delay(s) according to an aspect of the present disclosure. As depicted in that Figure, a single receiver 410 is employed and SS-OCT information from each optical fiber comprising the multi-core fiber 425 is extracted through the utilization of distinct delays 414 (D Dn). By employing different delays in each fiber path, information about optical properties from each path is transformed into distinct intermediate frequencies (i.f.) at any photodetector(s) used. Such an approach of encoding two signals into different i.f. frequencies has been employed in polarization sensitive OCT (PS-OCT) but has not—prior to the present disclosure—been employed in optical endoscopes and in particular not in conjunction with multi-core optical endoscopes according to the present disclosure.

As may be appreciated with continued reference to FIG. 4, DSP unit 417 may process these n distinct i.f. frequencies as they arrive as different—and substantially non-overlapping—frequency bands. Those skilled in the art will readily appreciate that such a configuration results in considerable advantage over the prior art as it utilizes only one receiver and exhibits only a 1/n loss in reflected signal power and transmitted power. Note further that while this illustrative configuration is shown, those skilled in the art will now appreciate from this disclosure that alternative configurations according to the present disclosure may be constructed that achieve the same result(s).

Similar to the system shown previously with respect to FIG. 3, the receiver 410 is coupled to the endoscope 430 by the multicore optical fiber 425, wherein each of the individual fibers comprising the multicore optical fiber includes one or more distinct delay elements 414 (D . . . . Dn) which produces a distinct delay for each of the individual fibers. The endoscope 430 generally includes a body—providing a protective and structural jacket 440 to the multicore fiber 425 as well as other elements positioned therein and comprising the overall endoscope 430. Notably, distal optics 470 produce optical scan beams 480 and is generally protected through the effect of cap, 460. As will become apparent to those skilled in the art, a variety of distal optical configurations are contemplated according to the present disclosure.

Figure 5:
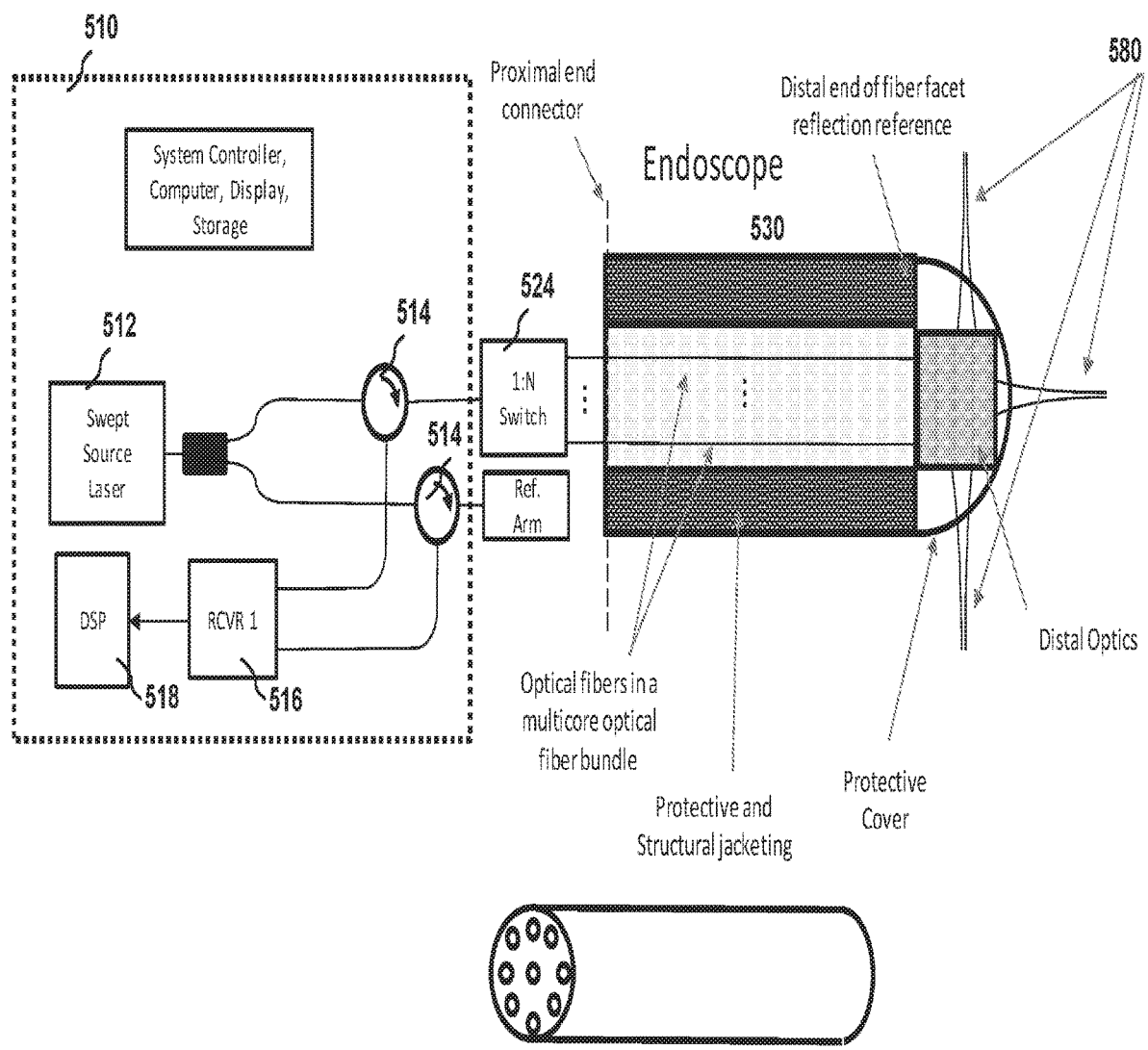
FIG. 5 shows a schematic diagram of another multi-core fiber endoscope employing a single SS-OCT receiver and 1:N switch(es) interconnecting the receiver to the endoscope according to an aspect of the present disclosure.

FIG. 5 shows yet another illustrative embodiment of a multi-core optical endoscope system 500 according to the present disclosure wherein an illustrative SS-OCT sub-system 510 is coupled to a multi-core optical fiber endoscope sub-system 530 through the effect of a 1:N switch 524. As depicted in that Figure, the illustrative sub-system 510 includes a number of circulators 514 along with receiver 516 and DSP 518 for receiving and processing return signals from samples illuminated by beams 580 and under examination by endoscope system 500. In a particular illustrative embodiment of the system 500 shown in the Figure, repetition rate of laser 512 may be synchronized to the switching rate of the 1:N switch 524 such that light is transmitted and received substantially during a single frequency sweep (or multiple thereof). In this manner, inefficiencies associated with switching dynamics are incurred during a period when the laser is blanked—at lower power. In this manner, unused portion(s) of the laser frequency sweep is overlapped in time with unusable portions of the switching during switching transients.

With this disclosure, those skilled in the art will readily appreciate that this approach has the advantage of higher optical sensitivity as all of the laser light and sample reflected light is coupled to one (or more) of the optical fibers comprising the multi-core optical fiber. As noted previously, other alternative optical systems and components such as spectral-domain OCT, time-domain OCT, confocal systems, fluorescence sensors, Raman sensors and other may be used in place of the SS-OCT system shown illustratively. Of course, the SS-OCT system including the 1:N switch may be constructed using integrated optical technologies—e.g. silicon photonics—to achieve a compact, reliable, low-cost system. Similarly—and as noted previously—these same techniques/structures/methodologies may be employed with any/all of the illustrative examples disclosed herein.

Figure 6:
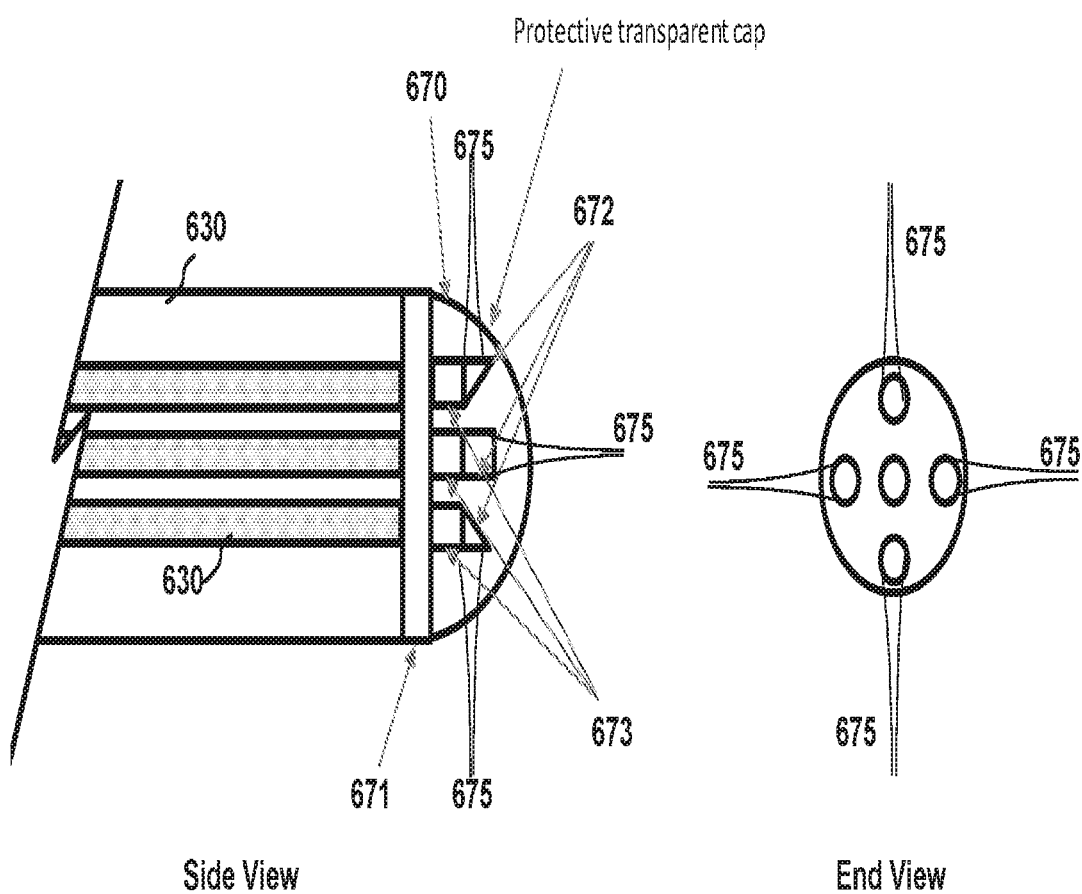
FIG. 6 shows a schematic diagram of an illustrative distal portion of a five-core optical fiber endoscope according to an aspect of the present disclosure.

Turning now to FIG. 6, there is shown in schematic form another illustrative embodiment (both side and end view(s)) of a distal end of multi-core fiber endoscope 600 according to an aspect of the present disclosure. As may be observed from that Figure, the distal end of the endoscope includes a protective cap 670 and distal optics including collimating lens(es) 673, fold mirrors 672, and substrate 671 coupled to the multi-core fiber, 625 which in this illustrative embodiment includes 5 (five) single optical fibers shown arranged as a central fiber with four perimeter fibers. Of course, those skilled in the art will appreciate that the number of individual fibers and number(s) of individual distal optical elements may be changed as specific application needs dictate. Additionally, the arrangement of the individual fiber(s) and distal optical element(s) may change from application to application as well. Shown further in that Figure is the light beam patters 675 which emanate from the distal optics.

With continued reference to FIG. 6—and as will be appreciated by those skilled in the art—certain details of structural and protective jacket (body) of the endoscope is not shown for simplicity. Operationally, light emanating from each fiber core is collected and directed into tissue/structures through the effect(s) of lens(es) 673 and mirrors 672. Notably, while the term "mirrors" is used herein—the disclosure is not so specifically limited. Other optical structures which redirect and/or the light in a desired manner such as prisms, light guides, photonic integrated circuits, etc., are contemplated for such structures and purpose as well.

Accordingly, there exist numerous approaches to the distal optics of a multi-core fiber optic endoscope according to the present disclosure. In particular, lens(es) may be graduated index (GRIN) lenses, ball lenses, fiber lenses, and/or lens arrays including multimode, multicore fiber lens that may be affixed or fusion spliced to the distal end of the multi-core fiber. Optional fold mirrors (or prisms or other structures) may be used to redirect light from optical fiber core(s) substantially away from endoscope axis—as desired. Also, one or more center cores may be coupled to optical structures (lenses, etc) that direct light substantially along the endoscope axis.

Advantageously, and as will be readily appreciated by those skilled in the art, all distal optical elements—or selected components thereof—may be made from discrete components, one or more molded components, photonic integrated circuit(s) or combinations thereof. As shown in the Figure(s), a protective cap may be fully or partially transparent or include windows to allow light to traverse from optical fibers and/or optical elements to/from samples under examination while providing a smooth, sufficiently strong, and appropriately shaped character such that it may be presented/inserted/retrieved from anticipated pathways such as the interior of a bodily lumen. Furthermore—as shown in FIG. 6, the entire distal optics may be assembled and/or fabricated as part of or on top of a substrate. Advantageously, the substrate may allow beam expansion from fiber to lens(es) such that a desired focus, beam waist etc. may be realized. As an illustrative example—and not considered limiting—if a multicore fiber is operating in a single mode regime at 1300 nm, then the core size is ~9 um. As is known in the art, to a achieve a ~20 um beam waist ($1/e^2$) at a ~1 mm focal length requires ~28 um diameter ($1/e^2$) at a face of a lens (in air). Longer focal lengths require a correspondingly larger beam diameter at the lens face where requires a larger lateral separation between fiber cores in the multicore fiber. As may be appreciated, it is desirable that light propagating along the fiber cores and up to and out of any lense(s) does not have substantial leakage from one channel to another.

Of further note, alternative illustrative embodiments of the arrangement of FIG. 6 may not necessarily include the lens(es) depicted in that Figure. In particular, one or more fold mirrors may be employed to redirect light into/away from the fiber axes—as appropriate. Advantageously, such a configuration is not only simple, but limited imaging range may be achieved (~0.3 um the Rayleigh range assuming a 1310 nm wavelength and a ~9 um beam waist at fiber facet). Accordingly—and as will be readily understood by those skilled in the art—there are a variety of other focal length/focal spot size width exit beam diameter design tradeoffs that may be made depending on the desired operating parameters.

As may be appreciated, there are many medical and non-medical applications that would benefit from a simple, low-cost, compact, reusable and/or disposable endoscope such as one(s) constructed according to the present disclosure. Such applications include where a precise, continuous profile of an intimal surface of a lumen is not needed but a measurement of 2, 4, or 8 cross sectional dimensions of the lumen opening is sufficient. For example, when using a nine core optical fiber with one fiber as a central fiber and eight fibers positioned concentrically around the perimeter of that central fiber—each perimeter fiber having a fold mirror associated with it—then four cross-sectional measurements along the 0, 45, 90 and 135 degree axis may be made along with one forward axial measurement. Such measurement(s) may be combined with fiber pull-back mechanism(s) to pull (or push) the endoscope substantially along the axis of the fiber. As will be shown and discussed, it is possible to perform a manual or automated twisting action—back and forth—to sample more of the circumferential area of interest. In this manner four cross-sectional measurements may continuously be made as the endoscope/fiber is pulled back. Such measurement(s) may be useful for a variety of applications including sizing lumens for stents or other therapeutic or interventional procedures. Of further advantage, such endoscope(s) may be combined with other measurement devices/techniques including optical measurements (fluorescence, NIR, Raman) or non-optical devices (e.g., pressure, temperature, pH, etc.) It is also possible to combine such device(s) with therapeutic devices such as surgical lasers, cryo or RF ablation, mechanical cutting tools, and/or other devices/structures. Of distinct advantage, it is possible to position such devices within the inside of a needle—due to its small size.

Figure 7A:
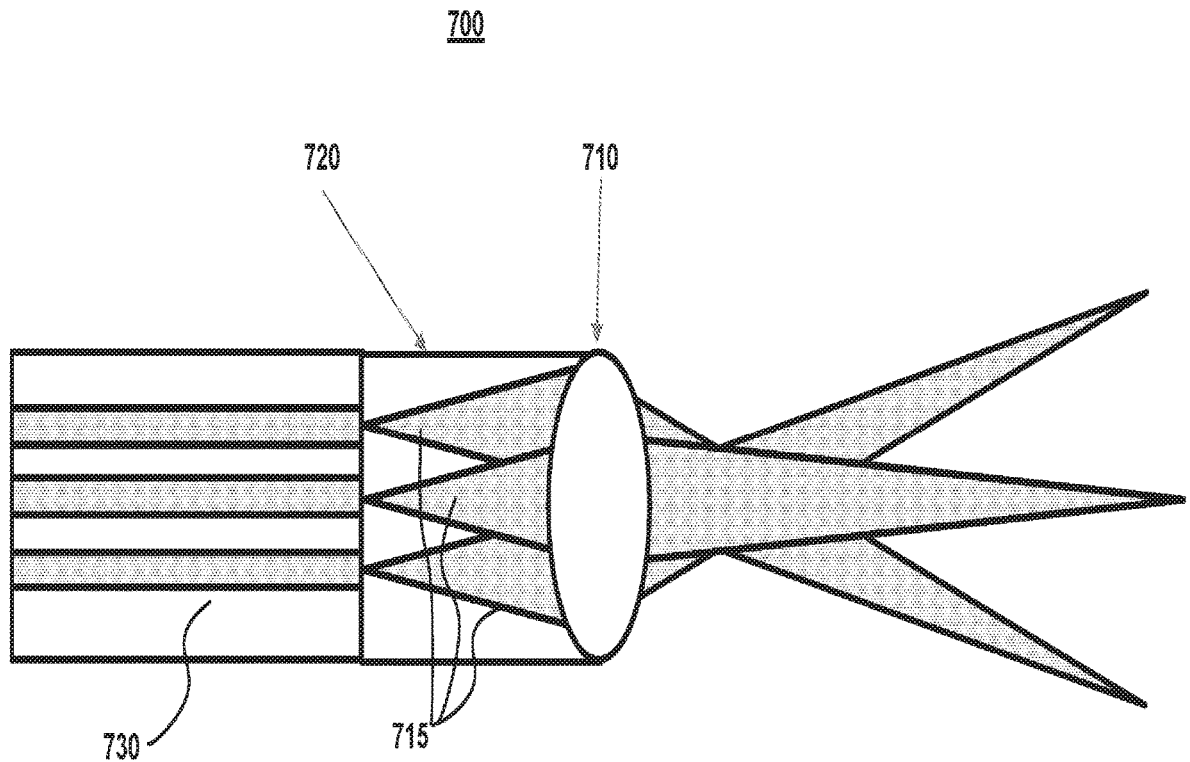
FIG. 7(A), FIG. 7(B), FIG. 7(C), FIG. 7(D) and FIG. 7(E) show a series of illustrative arrangements as schematic diagrams other illustrative multi-core fiber endoscope employing.

FIG. 7(A), FIG. 7(B), FIG. 7(C), FIG. 7(D) and FIG. 7(E) show a series of illustrative arrangements as schematic diagrams other illustrative multi-core fiber endoscope employing: FIG. 7(A) a collimating lens, FIG. 7(B) a fiber/lens coupling element including a passive or active beam steering elements, FIG. 7(C) a graduated index (GRIN) lens or section of multimode fiber, FIG. 7(D) a multi-element collimating lens, and FIG. 7(E) a beam deflector element—as part of distal optics all according to certain aspects of the present disclosure.

More particularly FIG. 7(A) shows another illustrative example of a multi-core fiber endoscope 700 according to the present disclosure wherein a single, shared collimating lens 710 is employed to collimate multiple outputs 715 from multi-core optical fiber 730. Advantageously, the lens may be a single element lens that is coupled to the multi-core fiber 730 via a free-space or solid coupling mechanism(s) 720 including direct fusion splice of a graded index lens constructed of optical fiber or cementing a GRIN lens to the end of the multi-core fiber. Of further advantage, the lens so coupled may be a single element or multiple, separate elements. Such lens(es) may be a GRIN lens, ball lens or aspheric molded glass lens—among other types as well. One additional possibility is the construction of lensing element(s) using fiber gratings within the core or cladding material of the multi-core fiber.

Figure 7B:
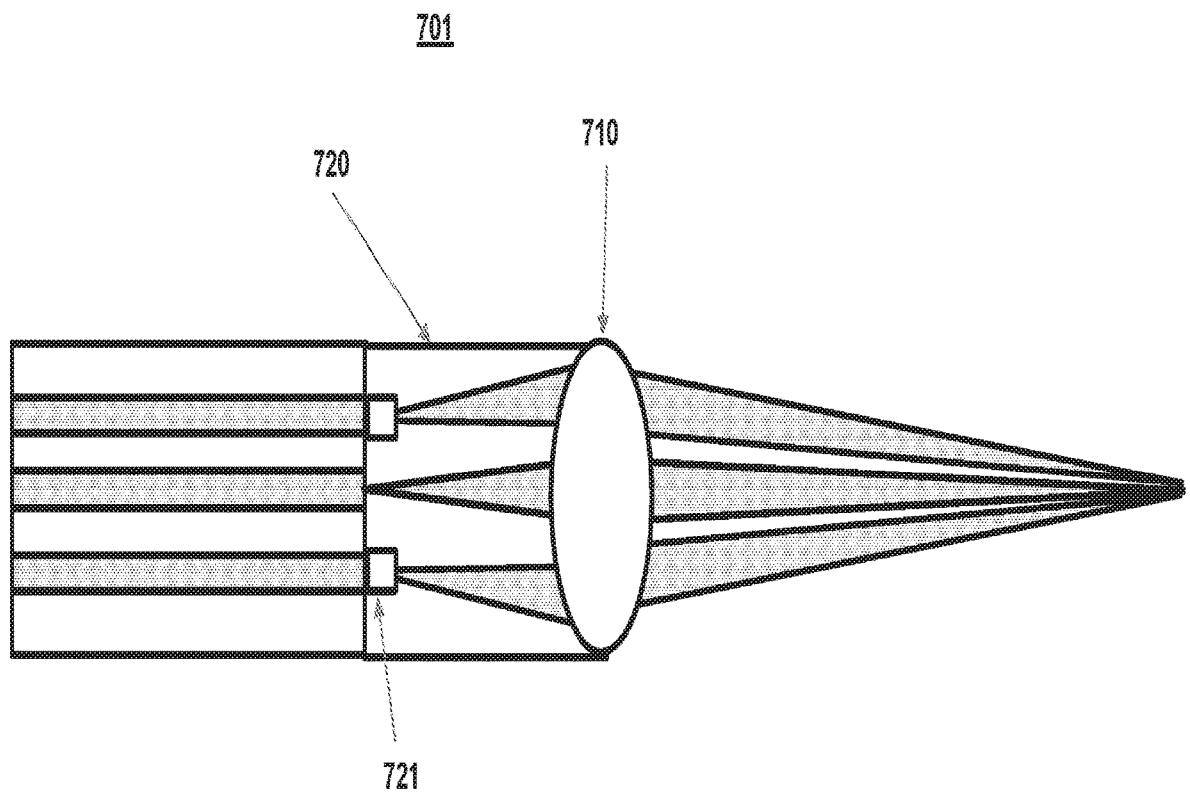

With reference now to FIG. 7(B), there is shown yet another illustrative example of a multi-core fiber endoscope 701 according to an aspect of the present disclosure wherein a fiber/lens coupling element 720 includes a passive or active beam steering element(s) 721, i.e., a prism element, to adjust the focus location of light emanating from each of the individual fibers comprising the multi-core fiber (shown emanating onto a collimating lens 710) such that the focus location(s) are nearly identical with respect to any sample(s) being examined.

Advantageously, there are a number of approaches to this illustrative example. In particular, if there are N cores in the multi-core fiber then all N cores may be utilized in parallel using receiver structure(s) shown previously. Alternatively, if only a single fiber—for example the center fiber—emits light and the remaining fibers—or a subset of the remaining fibers—may simultaneously be used to collect light reflected from the sample(s). One particular advantage to this approach that will be readily appreciated by those skilled in the art is that beam waists are in the same—but not necessarily exact same) location and additional information about angular scattering and back reflection of light from the sample may be obtained and used to differentiate tissue structure. Of further advantage, using one (or more) of the individual fibers comprising the multi-core optical fiber to illuminate and using other fibers to collect light reflected from the sample(s) may be extended to any of the embodiments contemplated herein or derivatives thereof.

Figure 7C:
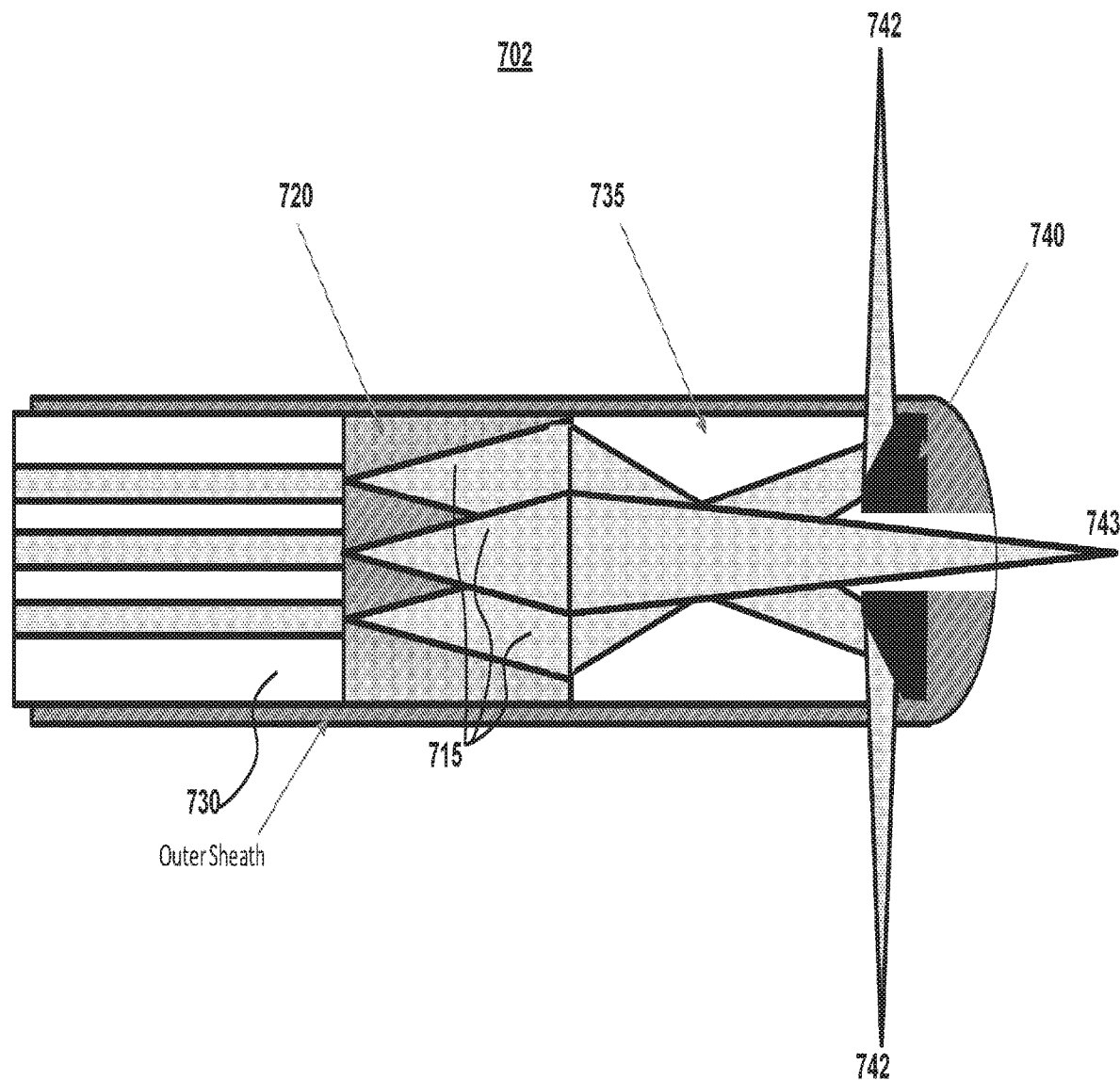

FIG. 7(C) shows yet another illustrative embodiment of a multi-core optical fiber endoscope 702 according to an aspect of the present disclosure. In particular, a lens employed may advantageously be a GRIN lens or a section of multimode fiber exhibiting a property to image facets of the multi-core fiber at an appropriate distal beam focus. The use of a multimode fiber, as is known in the art, is particularly attractive since it may be fusion spliced or otherwise easily secured to the end of the multicore fiber.

As may be appreciated, it is sometimes advantageous to use a section of coreless fiber positioned before the multimode fiber in the optical path to allow beam(s) to more freely expand. Once the beam diameter is of sufficient size to achieve the focal depth and confocal parameter the beam may enter a beam propagation region 735. Once the beam(s) are sufficiently spatially separated an optional distal beam deflector 740 element can be used to deflect some of the beams 742 substantially away from the axis of the endoscope and allow one or more or no beam to pass through substantially uninterrupted to allow for forward ranging 743. The endoscope can have transparent windows at appropriate beam exit locations and as noted previously—when smooth—allows for easier insertion into tight spaces. Similarly, an outer sheath of the endoscope body may be made transparent and constructed from a biocompatible materials. Finally, it is noted that while the particular application of the principles provided in this disclosure have used endoscopes as examples, the disclosure is not so limited. In particular, aspects of this disclosure will apply equally well to using sensors and imaging within catheters, guidewires, needles, laparoscopes and other medical—and non-medical—devices.

Figure 7D:
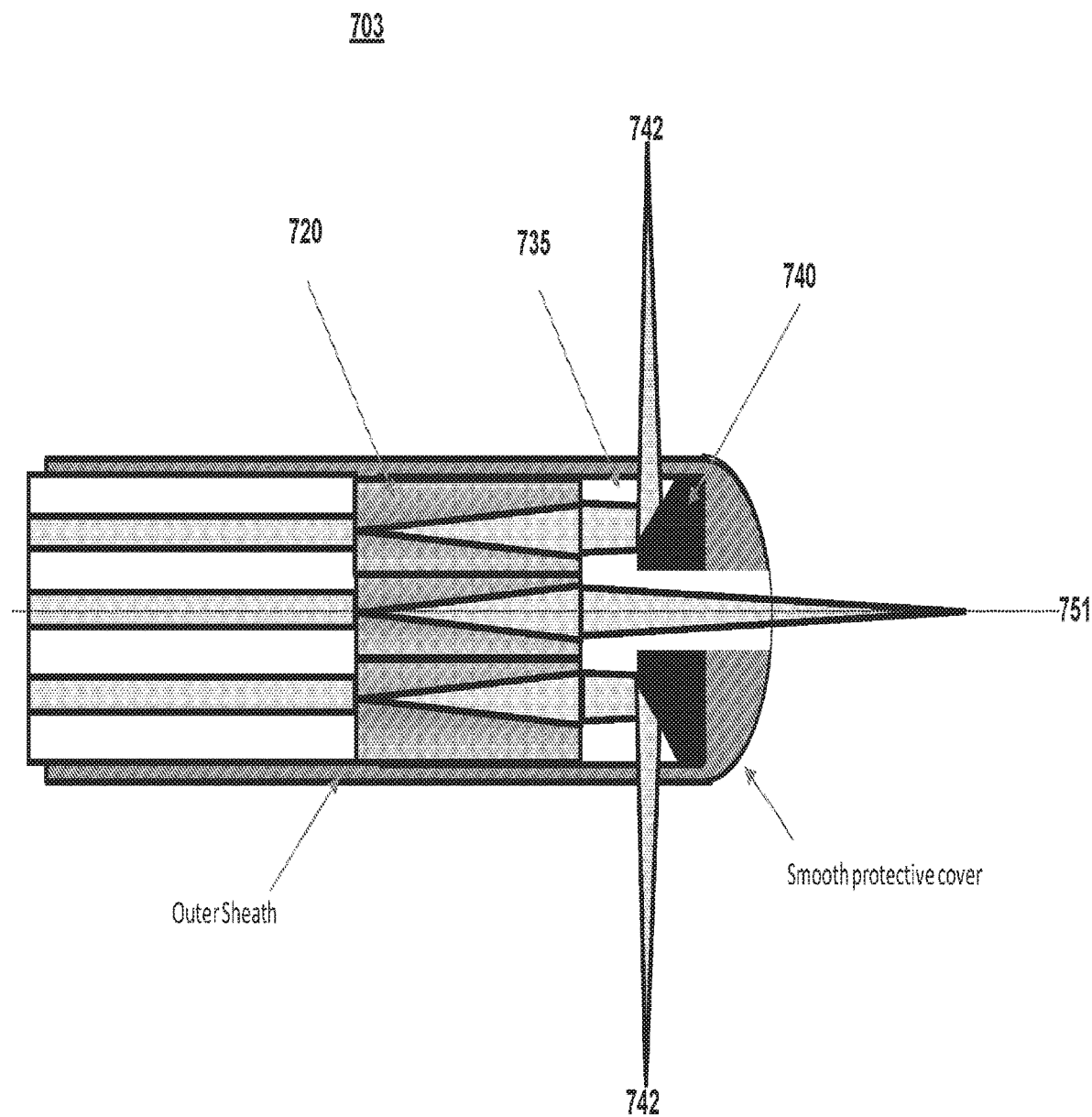
Figure 7E:
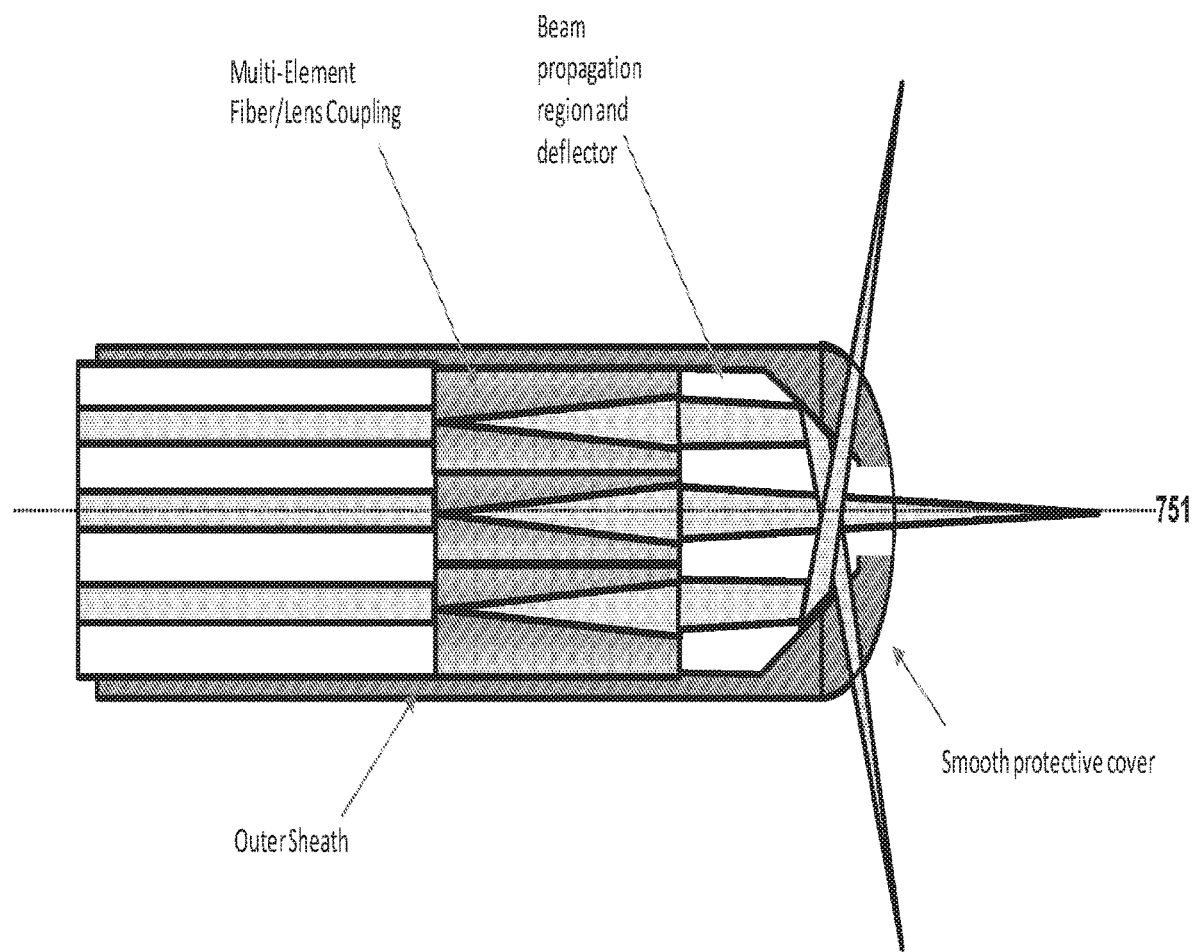

FIG. 7(D) shows yet another illustrative embodiment of a forward imaging multicore fiber endoscope 703 having a multi-element collimating lens and distal beam deflector element 740. More particularly—and as depicted in that Figure—a multi-element fiber/lens coupling element 720 is employed to individually collect light from each of the individual multicore fiber outputs 715 and direct/focus it such that the light may be more particularly directed onto/into a sample (not specifically shown). In a particular illustrative embodiment, such multi-element fiber/lens coupling element 720 may comprise a multi-mode, multicore optical fiber that is fusion spliced or otherwise connected to a single mode multi-core fiber. In an illustrative embodiment, the outside diameter of the multi-mode multicore fiber is substantially the same as the outside diameter of the single-mode multicore fiber. Of course, other applications may advantageously utilize configurations in which the outer diameters are not the same—for example, those applications in which a larger exit beam diameter is desired.

With continued reference to FIG. 7(D), it may be observed that in an illustrative embodiment the multi-mode multi-core fiber is configured with an appropriate GRIN-like profile to achieve appropriate beam parameters for example, focal distance, confocal parameter, etc. for imaging light onto/into the sample (not specifically shown). Additionally, it may be observed that the illustrative embodiment shown in the FIG. 7(E) includes a beam deflector element, that is configured to direct one or more light beams 742 in a direction substantially away from the endoscope axis 751 such that they may be directed to the sample.

Figure 8:
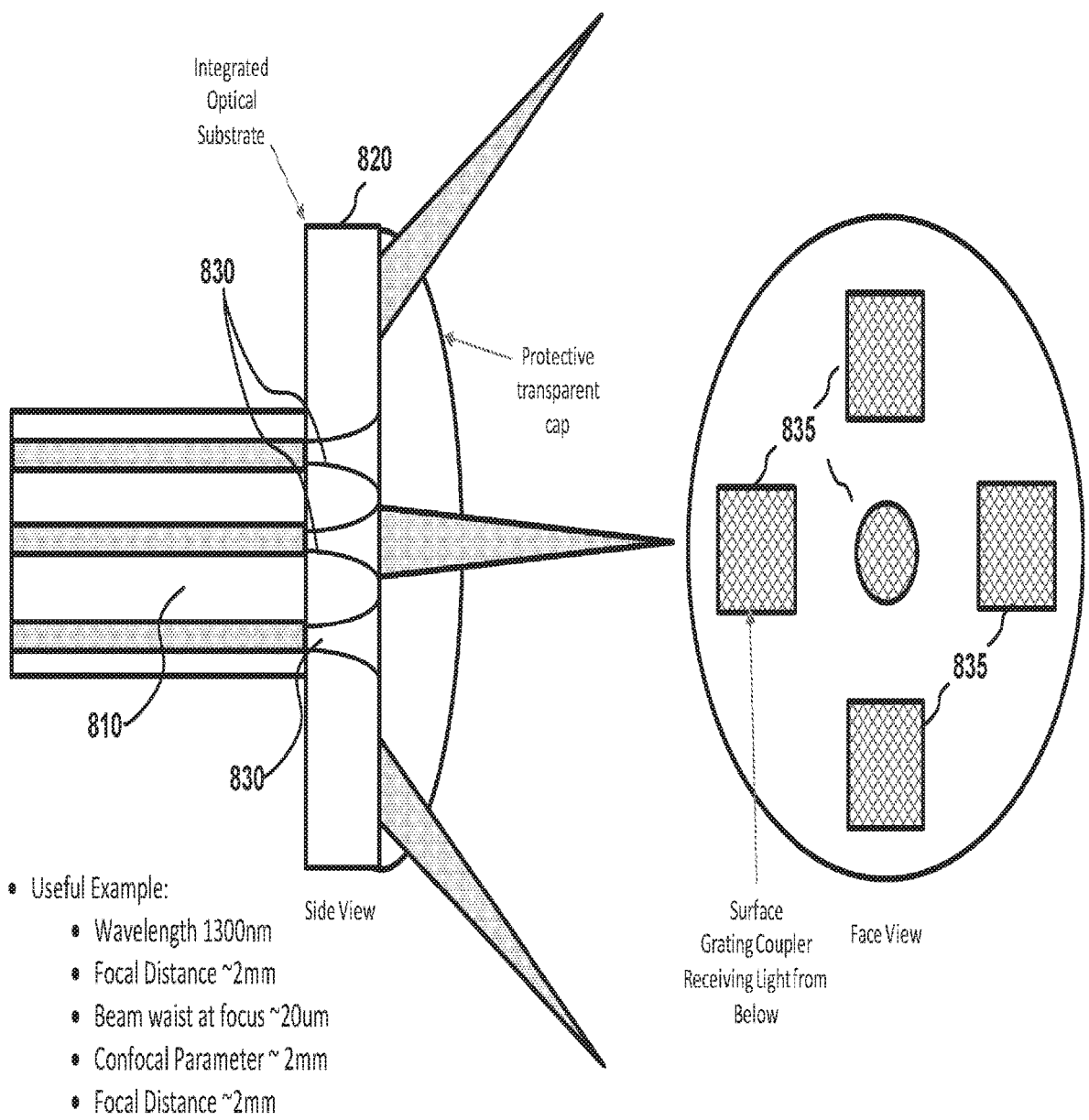
FIG. 8 shows a schematic diagram of an illustrative multi-core fiber endoscope wherein the multi-core fiber is connected to a photonic integrated circuit (PIC) according to an aspect of the present disclosure.

FIG. 8 shows yet an additional illustrative example according to the present disclosure in which a multicore fiber 810 is coupled to a photonic integrated circuit (PIC—or Integrated Optical Substrate) 820. As will be readily appreciated by those skilled in the art, there exist a wide variety of PIC technologies and materials including PLC, InP and the entire family of Silicon Photonics materials. As depicted in the Figure, light from the multicore fiber 810 is butt coupled to the integrated optic substrate through which it propagates via light guides 830 formed therein, and subsequently impinges on respective surface grating coupler(s) 835. Those skilled in the art will readily understand and appreciate the operation of 1D and 2D surface grating couplers and that any among a variety of same may advantageously be employed in structures according to the present disclosure. Further appreciated, is the fact that the surface grating couplers individually collect diverging light from each of the fibers in the multicore fiber and simultaneously reemit it in such that it is directed into a sample (not shown). Conversely, such surface grating coupler(s) operate in the reverse direction by collecting light from sample(s) and directing it to the fibers comprising the multicore fiber.

Figure 9:
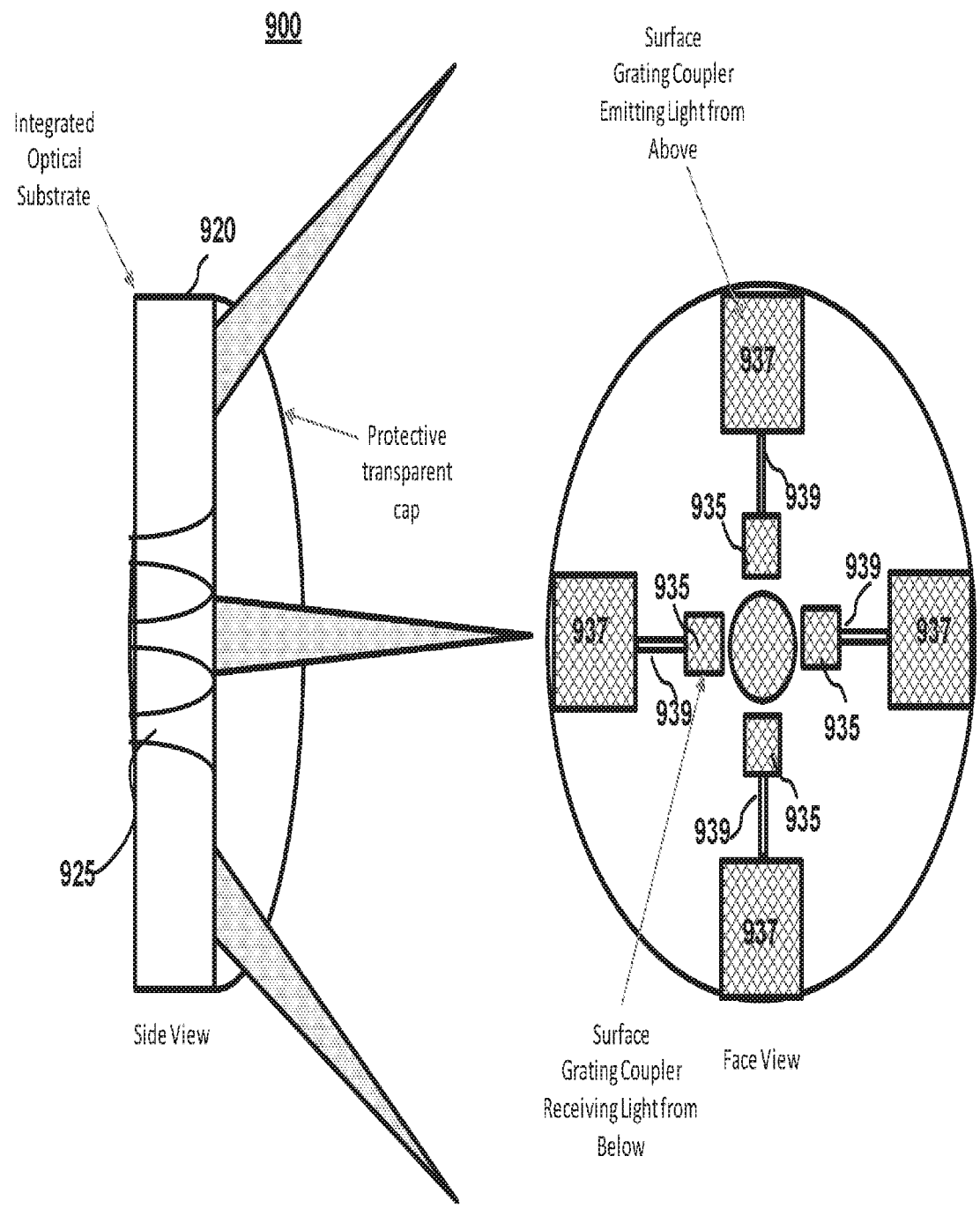
FIG. 9 show another schematic diagram illustrating a multi-core fiber endoscope wherein the multi-core fiber is connected to a PIC according to an aspect of the present disclosure.

Turning now to FIG. 9, there is shown an additional illustrative example of multicore optical fiber endoscope distal end 900 according to yet another aspect of the present disclosure. More particularly and as depicted in that Figure, the multicore optical fiber 930 is shown coupled to a photonic integrated circuit 920. As depicted therein, light from the multicore fiber (not specifically shown)—which is butt coupled to the integrated substrate of the PIC 920 wherein it propagates via waveguide structures 925 to one or more surface grating coupler(s) 935. As depicted in this illustrative example, inner grating couplers 935 couple light to/from the waveguides 930 and multicore optical fiber as well as additional waveguides 939 which convey light from inner couplers 935 to/from outer surface grating couplers 937 which emit/receive light to/from sample(s).

For simplicity, only a single waveguide is shown connecting optical fibers to respective inner surface grating couplers and subsequently to outer grating couplers. Notably, two or more waveguides may be employed to couple the optical fibers to the inner grating as well as two or more waveguides to couple the inner grating couplers to the outer grating couplers such that one or two polarization modes are conveyed. Note further that the number of waveguides connecting the couplers does not have to be the same for each. As will be appreciated, configurations according to the present disclosure such as that shown in FIG. 9 provide an advantage namely that the radius of the multicore fiber employed may be smaller and still provide a large aperture on emitting surface grating coupler.

Figure 10:
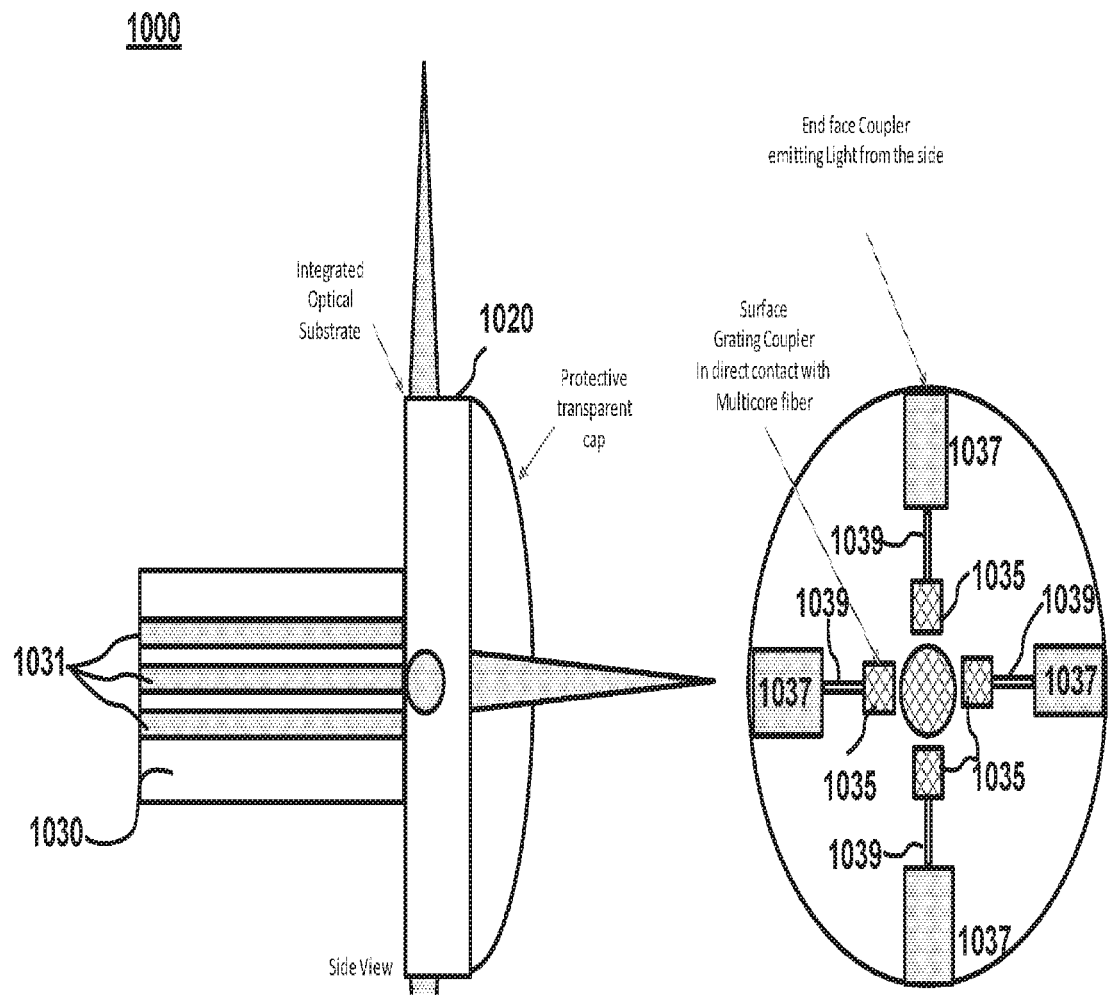
FIG. 10 shows yet another schematic diagram illustrating a multi-core fiber endoscope wherein the multi-core fiber is connected to a PIC according to an aspect of the present disclosure.

FIG. 10 shows yet another illustrative example according to the present disclosure of a multicore optical fiber endoscope configuration 1000 wherein the multicore optical fiber 1030 is coupled to a photonic integrated circuit (integrated optical substrate) 1020. Here, the individual cores 1031 of the multicore fiber 1030 are directly butt coupled to a surface grating coupler(s) 1035 fabricated in/on the circuit substrate 1020. The surface grating coupler(s) so coupled to the fibers 1031 are further coupled to respective end facet emitter(s) 1037 via respective optical waveguide(s) 1039. As configured, the end facet emitter(s) 1037 emit light substantially orthogonally to the axis of the multicore fiber (except for a center core). As will be understood and appreciated by those skilled in the art, there exist a number of end facet (horizontal) couplers that may be used including adiabatic coupling approaches. Advantageously—with a configuration such as that depicted—if the wavelength employed is 1300 nm and a focal distance of 2 mm is desired, with a beam waist of ~20 um, then a beam waist at the exit facet is ~46 um.

At this point it is noted that a number of the illustrative embodiments shown exhibit a central fiber comprising the multicore fiber which is shown in the Figures to emit light along the axis of the fiber (forward). As will be appreciated, such emission—while desirable in certain applications—is not necessary in all. Additionally, it is noted that the individual fibers comprising the multicore fiber do not all have to be the same. In particular, a combination of different fibers may be employed where—for example—some fibers are single mode while others are multimode fibers. Further, some of the fibers may be employed for imaging and sensing while others may be used for invasive or other therapeutic procedures or other diagnostic modalities.

As will be appreciated, in many optical systems, including OCT systems, there is a tradeoff made between the measurement range (e.g. the confocal parameter or 2× the Rayleigh Range) and the resolution at the beam waist. Generally, the tighter the beam waist, the higher the lateral resolution but the shorter the measurement range. One of the attractive features of PIC and other integrated optical designs is that by using the high-resolution lithographic techniques for manufacturing the PICs one can make very complex amplitude and/or phase masks in the surface gratings.

For example, Bessel beam generation, and other similar depth-of-filed extension techniques, may be designed into the phase mask to provide extended measurement range for a given lateral resolution. Such depth-of-field extension techniques, can be designed into the surface grating couplers using PIC design tools and are advantageously applicable embodiments according to the present disclosure shown and described.

As noted previously, one of the advantages of using a multicore fiber is that it allows several simultaneous beams to be guided up/down the endoscope for sensing, imaging, and ranging. One application of such an endoscope acquires several readings of an interior dimensions of a lumen and/or measures properties of interest of the lumen wall. While a single core configuration having a distal motor or a rotating fiber (as is known in SS-OCT cardiovascular and gastroenterology systems) can produce a continuous measurement of a lumen, such an approach comes with noted disadvantages including increased cost, size, and complexity of the endoscopic probe. Multicore fiber configurations according to the present disclosure have the potential to be smaller and therefore be employed into tighter lumens and medical devices (e.g. imaging needles).

Figure 11:
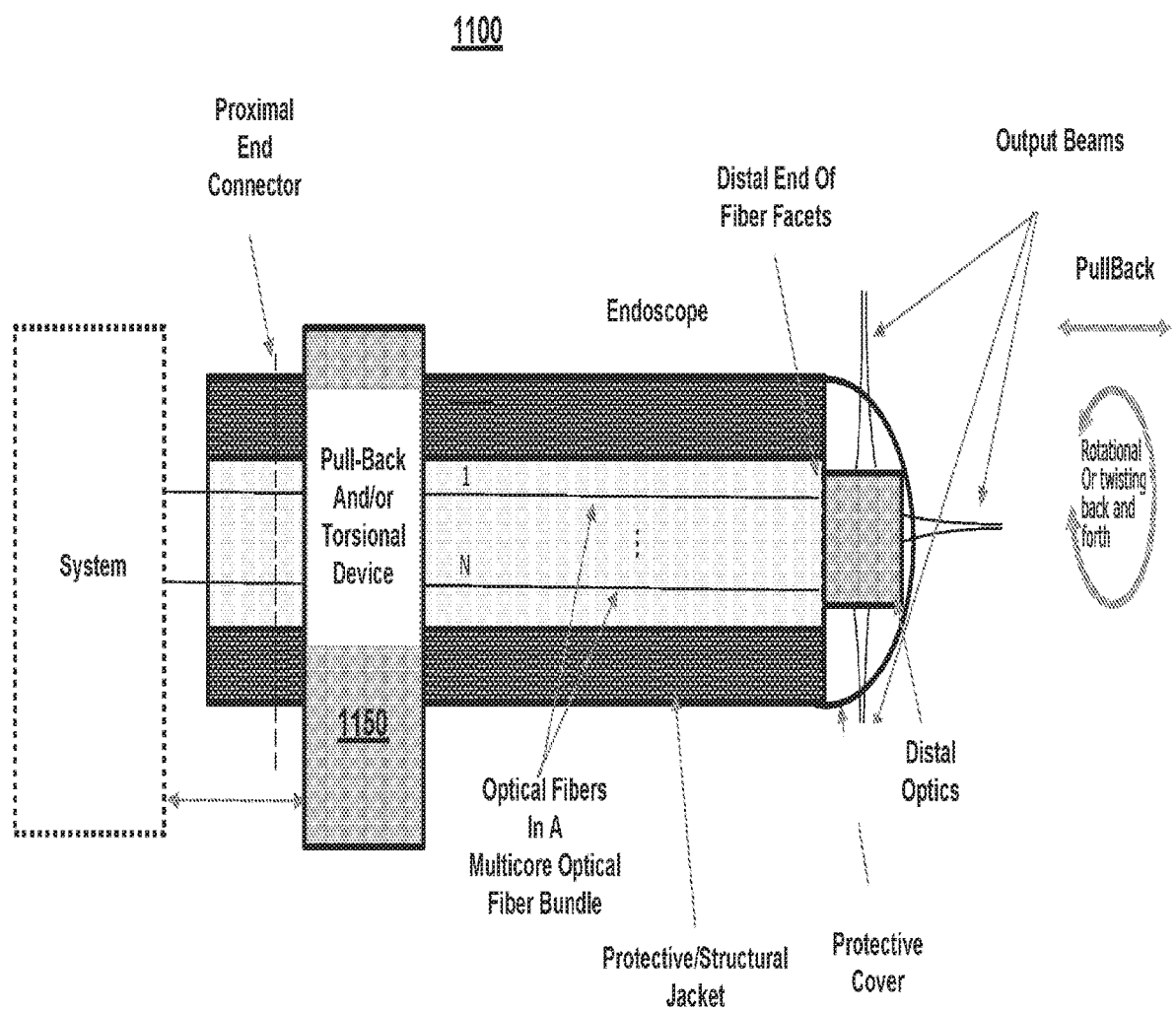
FIG. 11 show a schematic diagram illustrating a multi-core fiber endoscope having a pull-back and/or rotational or twisting proximal motor according to an aspect of the present disclosure.

Of further advantage, it is possible to include additional measurement or imaging capability to multi-core fiber endoscopes constructed according to the present disclosure. Turning now to FIG. 11 there is shown a multicore fiber endoscope 1100 including a pull-back (or push-back) and/or torsional element 1150 Such an element allows for the manual and/or automated pulling-back (or pushing forward) of the distal end of the endoscope along the axis of the endoscope body and lumen in which it is positioned. In this manner, optical measurements may be made along the axis of the lumen which advantageously allows several two-dimensional images to be obtained. Alternatively, and in another illustrative embodiment, the entire multi-core fiber may be rotated back and forth (to and fro) as to radially scan the distal end of the endoscope and therefore the lumen/sample. This advantageously allows additional regions of the sample to be measured. It is also contemplated to have both pullback capability and twisting back and forth capability.

Note further that illustrative embodiments according to the present disclosure have depicted a number of ways to image light from a multicore fiber into a sample. There are of course other methods and combinations of the methods shown that may be implemented and are contemplated herein. Additionally, there are also many other aspects of a fiber endoscope design known in the art while not specifically shown and described. Such aspects include protective jackets (metal or plastic), torque cables, markers for x-ray, CT, or MM imaging, etc. With this disclosure and teachings in place, those skilled in the art will readily understand and appreciate that there are numerous applications of structures and techniques according to the present disclosure in addition to SS-OCT and endoscopes including—but not limited to—catheters, guidewires, imaging needles, laparoscopes, and other medical and non-medical devices.

At this point those skilled in the art will readily appreciate that while the methods, techniques and structures according to the present disclosure have been described with respect to particular implementations and/or embodiments, those skilled in the art will recognize that the disclosure is not so limited. Accordingly, the scope of the disclosure should only be limited by the claims appended hereto.

The invention claimed is:

1. An optical instrument comprising:
    a) an optical source that generates an optical beam at an output;
    b) a multicore fiber comprising an input optically coupled to the output of the optical source and comprising at least two optical fiber cores that are configured to deliver and collect light from a sample located external to the multicore fiber;
    c) fixed distal optics optically coupled to a distal end of the multicore fiber, the fixed distal optics configured such that light from one of the at least two optical fiber cores is directed in a first fixed direction with respect to an axis of the multicore fiber and light from the other of the at least two optical fiber cores is directed in a second fixed direction with respect to the axis of the multicore fiber wherein the first fixed direction and the second fixed direction are different and
    d) a receiver having an input optically coupled to each of the at least two optical fiber cores, the receiver configured to receive light collected from the sample and interferometrically combine the received light collected from the sample with light collected from a reference path,
    wherein the interferometrically combined light from the different optical fiber cores having traversed different optical delays along their path from source to interferometric combining such that the interferometrically combined light from the different optical fibers cores show up in parallel at different intermediate frequencies (I.F) when converted into an electrical signal, so that an intermediate frequency is associated with light directed in the first fixed direction with respect to the axis of the multicore fiber and a different intermediate frequency is associated with light directed in the second fixed direction with respect to the axis of the multicore fiber, and so that the electrical signal can be separated and processed to yield information about the sample from measurements at two different fixed directions with respect to the axis of the multicore fiber.

2. The optical instrument of claim 1 wherein each of the at least two fiber cores operate as a single mode fiber at the wavelengths of light of the optical source.

3. The optical instrument of claim 2 wherein the optical source comprises a swept source laser.

4. The optical instrument of claim 2 wherein the receiver comprises a dual-balanced optoelectronic receiver.

5. The optical instrument of claim 2 wherein the receiver comprises a dual-balanced and dual-polarization optoelectronic receiver.

6. The optical instrument of claim 2 wherein the receiver comprises a photonic integrated circuit (PIC).

7. The optical instrument of claim 1 further comprising a pull-back element configured to pull back a distal end of the optical instrument.

8. The optical instrument of claim 1 wherein the first fixed direction comprises a fixed direction substantially away from the axis of the multicore fiber and the second fixed direction comprises a fixed direction substantially along the axis of the multicore fiber.

9. The optical instrument of claim 8 wherein the first fixed direction comprises a direction with an axis having an angle of 45-degrees away from the axis of the multicore fiber.

10. The optical instrument of claim 8 wherein the first fixed direction comprises a direction with an axis having an angle of 90-degrees away from the axis of the multicore fiber.

11. The optical instrument of claim 8 wherein the first fixed direction comprises a direction with an axis having an angle of 135-degrees away from the axis of the multicore fiber.

12. The optical instrument of claim 8 wherein the electrical signal being separated and processed to yield information about the sample from measurements at two different fixed directions with respect to the axis of the multicore fiber comprises the electrical signal being separated and processed to yield information about the sample from a forward axial measurement and a cross-sectional measurement.

* * * * *